US006579702B2

(12) United States Patent
Greenspan et al.

(10) Patent No.: US 6,579,702 B2
(45) Date of Patent: *Jun. 17, 2003

(54) MAMMALIAN TOLLOID-LIKE GENE AND PROTEIN

(75) Inventors: Daniel S. Greenspan, Madison, WI (US); Ian C. Scott, Madison, WI (US); Christina L. Thomas, Madison, WI (US)

(73) Assignee: Wiconsin Alumni Research Foundation, Madison, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/285,385

(22) Filed: Apr. 2, 1999

(65) Prior Publication Data

US 2002/0150946 A1 Oct. 17, 2002

Related U.S. Application Data

(60) Provisional application No. 60/111,873, filed on Dec. 11, 1998, and provisional application No. 60/080,550, filed on Apr. 3, 1998.

(51) Int. Cl.$^7$ .......................... C12N 15/12; C12N 5/10; C12N 1/21; C12N 15/00; C07H 21/04
(52) U.S. Cl. .................... 435/69.2; 435/325; 435/252.3; 435/320.1; 536/23.5; 536/23.1; 536/24.1; 530/350
(58) Field of Search ................. 435/69.1, 325, 435/252.3, 320.1, 69.2; 530/350; 536/23.2, 23.5, 24.3, 24.1

(56) References Cited

FOREIGN PATENT DOCUMENTS

| EP | 0 854 191 A2 | 12/1997 |
|---|---|---|
| WO | WO97/45528 | 12/1994 |

OTHER PUBLICATIONS

Li et al. Human (clone CTG–A4) mRNA sequence. GenBank Database Accession No. L10374, National Center for Biotechnology Information, Bethesda, MD. Jul. 26, 1993.*
Bowie et al. Deciphering the message in protein sequences: tolerance to amino acid substitutions. Science, (Mar. 16, 1990) 247 (4948) 1306–10.*
New England Biolabs 1995 catalog, p. 109.*
Janitz et al. Three alternatively spliceed variants of the gene coding for the human bone morphogenetic protein BMP–1. GenBank Database Accession No. Y08725, National Center for Biotechnology Information, Bethesda, MD. Feb. 24, 1997.*

Reynolds et al. Direct Submission. GenBank Accession No. U75331, National Center for Biotechnology Information, Bethesda, MD. Feb. 11, 1998.*

Panchenko, et al., "Metalloproteinase Activity Secreted by Fibrogenic Cells in the Processing of Prolysyl Oxidase," *The Journal of Biological Chemistry* 271:7113–7119 (1996).

Bond, Judith S. et al., "The Astacin Family of Metalloendopeptides," *Protein Science*, 4:1247–1261 (1995).

Crystal, Ronald, *Science*, 270: 404–409 (1995).

Greenspan, D.S., "Mus Musculus Mammalian Tolloid–like Protein mRNA", GenBank Accession No. U34042 (1996).

Johnson, George, "The Chicken with the Duck's Feet: It's All in the Biochemical Signal," *The New York Times Science* (May 21, 1996).

Kessler, Efrat, et al., "Bone Morphogenetic Protein–1: Type 1 Procollagen C–Proteinase", *Science*, 271: 360–362 (1996).

Mastrangelo et al., *Seminars in Oncology*, 23(1): 4–21 (1996).

Ngo, J. Thomas et al., in: The Protein Folding Problem and Tertiary Structure Prediction, 1994, Merz, K. Jr. et al., (ed.), Birkhauser, Boston, MA, pp. 433 and 492–495.

Takahara, Kazuhiko, et al., Bone Morphgenetic Protein–1 and a Mammalian Tolloid Homologue (mTld) Are Encoded by Alternatively Spliced Transripts Which Are Differentially Expressed in Some Tissues, *The Journal of Biological Chemistry*, 269(51): 32572–32578 (1994).

Takahara, Kazuhiko et al., "Structural Organization and Genetic Localization of the Human Bone Morphogenetic Protein 1/Mammalian Tolloid Gene", *Genomics*, 29(1): 9–15 (1995).

Takahara, Kazuhiko et al., "Characterization of a Novel Gene Product (Mammalian Tolloid–Like) with High Sequence Similarity to the Mammalian Tolloid/Bone Morphogenetic Protein–1", *Genomics*, 34(2): 157–165 (1996).

* cited by examiner

*Primary Examiner*—David S. Romeo
(74) *Attorney, Agent, or Firm*—Quarles & Brady LLP

(57) ABSTRACT

A mammalian gene encoding a tolloid-like protein distinct from human or murine BMP-1/mTld and distinct from human or murine mTll-1 is presented. The gene is similar in structure to members of the BMP-1 family of genes, but maps to a distinct location and encodes a distinct protein having distinct activities. The protein encoded by the gene can be used to screen putative therapeutic agents in an ongoing effort to inhibit activity of the BMP-1 family of genes to prevent scarring, fibrosis, and the like.

17 Claims, 3 Drawing Sheets

```
              1                                                           50
   htll-2   MPRATALGAL  VSLLLLLPLP  RGAGGLGER.  PDATADYSE.  LDGEEGTEQQ
   mtll-2   MPLATTLGTL  V.LLLLLPLP  RGAEVTGDH.  SNVALDYGA.  LEGEEGTEQQ
humtolloid  ~~~MPGVARL  PLLLGLLLLP  RPG.....R.  PLDLADYTY.  DLAEEDDSEP
      htll  ~~~MGLGTL   SPRMLVWLVA  SGIVFYGELW  VCAGLDYDYT  FDGNEEDKTE 51                                                         100
   htll-2   LEHYHDPCKA  AVFWGDIALD  EDDLKLFHID  KARDWTKQTV  GATGHSTGGL
   mtll-2   L.HYHDPCKA  AVFWGDIALD  EDDLKLFHID  KAEDWTKPSI  DKPGHDTGGL
humtolloid  L.NYKDPCKA  AAFLGDIALD  EEDLRAFQVQ  QAVDLRRHTA  RK........
      htll  TIDYKDPCKA  AVFWGDIALD  DEDLNIFQID  RTIDLTQNPF  GNLGHTTGGL 101                                                        150
   htll-2   EEQASESSPD  TTAMDTGTKE  AGKDGRENTT  LLHSPGTLHA  AAKTFSPRVR
   mtll-2   EE.TSARWPN  DTASNASIQA  PRKDGKDATT  FLPNPGTSNT  TAKTFSARVR
humtolloid  .SSIKAAVPG  NTSTPSCQST  NGQPQRGACG  RWRG......  .....RSRSR
      htll  GDHAMSKKRG  ALYQLIDRIR  RIGFGLEQNN  TVKGKVPLQF  SGQNEKNRVP 151                                                        200
   htll-2   RATTSRTERI  WPGGVIPYVI  GGNFTGSQRA  IFKQAMRHWE  KHTCVTFIER
   mtll-2   RATTSRTERI  WPGGVIPYVI  GGNFTGTQRA  IFKQAMRHWE  KHTCVTFVER
humtolloid  RAATSRPERV  WPDGVIPFVI  GGNFTGSQRA  VFRQAMRHWE  KHTCVTFLER
      htll  RAATSRTERI  WPGGVIPYVI  GGNFTGSQRA  MFKQAMRHWE  KHTCVTFIER 201                                                        250
   htll-2   TDEESFIVFS  YRTCGCCSYV  GRRGGGPQAI  SIGKNCDKFG  IVAHELGHVV
   mtll-2   TDEESFIVFS  YRTCGCCSYV  GRRGGGPQAI  SIGKNCDKFG  IVAHELGHVV
humtolloid  TDEDSYIVFT  YRPCGCCSYV  GRRGGGPQAI  SIGKNCDKFG  IVVHELGHVV
      htll  SDEESYIVFT  YRPCGCCSYV  GRRGNGPQAI  SIGKNCDKFG  IVVHELGHVI 251                                                        300
   htll-2   GFWHEHTRPD  RDQHVTIIRE  NIQPGQEYNF  LKMEAGEVSS  LGETYDFDSI
   mtll-2   GFWHEHTRPD  RDQHVTIIRE  NIQPGQEYNF  LKMEAGEVSS  LGETYDFDSI
humtolloid  GFWHEHTRPD  RDRHVSIVRE  NIQPGQEYNF  LKMEPQEVES  LGETYDFDSI
      htll  GFWHEHTRPD  RDNHVTIIRE  NIQPGQEYNF  LKMEPGEVNS  LGERYDFDSI 301                                                        350
   htll-2   MHYARNTFSR  GVFLDTILPR  QDDNGVRPTI  GQRVRLSQGD  IAQARKLYKC
   mtll-2   MHYARNTFSR  GVFLDTILPR  RDDNGVRPTI  GQRVRLSQGD  IAQARKLYKC
humtolloid  MHYARNTFSR  GIFLDTIVPK  YEVNGVKPPI  GQRTRLSKGD  IAQARKLYKC
      htll  MHYARNTFSR  GMFLDTILPS  RDDNGIRPAI  GQRTRLSKGD  IAQARKLYRC 351                                                        400
   htll-2   PACGETLQDT  TGNFSAPGFP  NGYPSYSHCV  WRISVTPGEK  IVLNFTSMDL
   mtll-2   PACGETLQDT  TGNFSAPGFP  NGYPSYSHCV  WRISVTPGEK  IILNFTSMDL
humtolloid  PACGETLQDS  TGNFSSPEYP  NGYSAHMHCV  WRISVTPGEK  IILNFTSLDL
      htll  PACGETLQES  NGNLSSPGFP  NGYPSYTHCI  WRVSVTPGEK  IVLNFTTMDL 401                                                        450
   htll-2   FKSRLCWYDY  VEVRDGYWRK  APLLGRFCGD  KIPEPLVSTD  SRLWVEFRSS
   mtll-2   FKSRLCWYDY  VEIRDGYWRK  APLLGRFCGD  KIPESLVSSD  SRLWVEFRSS
humtolloid  YRSRLCWYDY  VEVRDGFWRK  APLRGRFCGS  KLPEPIVSTD  SRLWVEFRSS
      htll  YKSSLCWYDY  IEVRDGYWRK  SPLLGRFCGD  KLPEVLTSTD  SRMWIEFRSS
```

FIG 1A

```
              451                                                          500
   htl1-2     SNILGKGFFA AYEATCGGDM NKDAGQIQSP NYPDDYRPSK ECVWRITVSE
   mtl1-2     SSSLGKGFFA VYEAMCGGDI TKDAGQIQSP NYPDDYRPSK ECVWRITVPD
 humtolloid   SNWVGKGFFA VYEAICGGDV KKDYGHIQSP NYPDDYRPSK VCIWRIQVSE
      htl1    SNWVGKGFAA VYEAICGGEI RKNEGQIQSP NYPDDYRPMK ECVWKITVSE 501                                                          550
   htl1-2     GFHVGLTFQA FEIERHDSCA YDYLEVRDGP TEESALIGHF CGYEKPEDVK
   mtl1-2     GFHVGLTFQS FEIERHDSCA YDYLEIRDGP TEDSTLIGHF CGYEKPEAVK
 humtolloid   GFHVGLTFQS FEIERHDSCA YDYLEVRDGH SESSTLIGRY CGYEKPDDIK
      htl1    SYHVGLTFQS FEIERHDNCA YDYLEVRDGT SENSPLIGRF CGYDKPEDIR 551                                                          600
   htl1-2     SSSNRLWMKF VSDGSINKAG FAANFFKEVD ECSWPDHGGC EHRCVNTLGS
   mtl1-2     SSANRLWVKF VSDGSINKAG FAANFFKEVD ECSWPDHGGC EQRCVNTLGS
 humtolloid   STSSRLWLKF VSDGSINKAG FAVNFFKEVD ECSRPNRGGC EQRCLNTLGS
      htl1    STSNTLWMKF VSDGTVNKAG FAANFFKEED ECAKPDRGGC EQRCLNTLGS 601                                                          650
   htl1-2     YKCACDPGYE LAADKKMCEV ACGGFITKLN GTITSPGWPK EYPTNKNCVW
   mtl1-2     YTCACDPGYE LAADKKTCEV ACGGFITKLN GTITSPGWPK EYPTNKNCVW
 humtolloid   YKCSCDPGYE LAPDKRRCEA ACGGFLTKLN GSITSPGWPK EYPPNKNCIW
      htl1    YQCACEPGYE LGPDRRSCEA ACGGLLTKLN GTITTPGWPK EYPPNKNCVW 651                                                          700
   htl1-2     QVVAPAQYRI SLQFEVFELE GNDVCKYDFV EVRSGLSPDA KLHGRFCGSE
   mtl1-2     QVVAPVQYRI SLQFEAFELE GNDVCKYDFV EVRSGLSPDA KLHGKFCGSE
 humtolloid   QLVAPTQYRI SLQFDFFETE GNDVCKYDFV EVRSGLTADS KLHGKFCGSE
      htl1    QVVAPTQYRI SVKFEFFELE GNEVCKYDYV EIWSGLSSES KLHGKFCGAE 701                                                          750
   htl1-2     TPEVITSQSN NMRVEFKSDN TVSKRGFRAH FFSDKDECAK DNGGCQHECV
   mtl1-2     TPEVITSQSN NMRVEFKSDN TVSKRGFRAH FFSDKDECAK DNGGCQQECV
 humtolloid   KPEVITSQYN NMRVEFKSDN TVSKKGFKAH FFSDKDECSK DNGGCQQDCV
      htl1    VPEVITSQFN NMRIEFKSDN TVSKKGFKAH FFSDKDECSK DNGGCQHECV 751                                                          800
   htl1-2     NTFGSYLCRC RNGYWLHENG HDCKEAGCAH KISSVEGTLA SPNWPDKYPS
   mtl1-2     NTFGSYLCRC RNGYRLHENG HDCKEAGCAY KISSAEGTLM SPNWPDKYPS
 humtolloid   NTFGSYECQC RSGFVLHDNK HDCKEAGCNH KVTSTSGTIT SPNWPDKYPS
      htl1    NTMGSYMCQC RNGFVLHDNK HDCKEAECEQ KIHSPSGLIT SPNWPDKYPS 801                                                          850
   htl1-2     RRECTWNISS TAGHRVKLTF NEFEIEQHQE CAYDHLEMYD GPDSLAPILG
   mtl1-2     RKECTWNISS TAGHRVKITF SEFEIEQHQE CAYDHLELYD GTDSLAPILG
 humtolloid   KKECTWAISS TPGHRVKLTF MEMDIESQPE CAYDHLEVFD GRDAKAPVLG
      htl1    RKECTWEISA TPGHRIKLAF SEFEIEQHQE CAYDHLEVFD GETEKSPILG 851                                                          900
   htl1-2     RFCGSKKPDP TVASGSSMFL RFYSDASVQR KGFQAVHSTE CGGRLKAEVQ
   mtl1-2     RFCGSKKPDP VVATGSSLFL RFYSDASVQR KGFQAVHSTE CGGRLKAEVQ
 humtolloid   RFCGSKKPEP VLATGSRMFL RFYSDNSVQR KGFQASHATE CGGQVRADVK
      htl1    RLCGNKIPDP LVATGNKMFV RFVSDASVQR KGFQATHSTE CGGRLKAESK
```

FIG 1B

```
                901                                                      950
     htl1-2    TKELYSHAQF GDNNYPSEAR CDWVIVAEDG YGVELTFRTF EVEEEADCGY
     mtll-2    TKELYSHAQF GDNNYPSQAR CDWVIVAEDG YGVELIFRTF EVEEEADCGY
  humtolloid   TKDLYSHAQF GDNNYPGGVD CEWVIVAEEG YGVELVFQTF EVEEETDCGY
       htll    PRDLYSHAQF GDNNYPGQVD CEWLLVSERG SRLELSFQTF EVEEEADCGY 951                                                     1000
     htl1-2    DYMEAYDGYD SSAPRLGRFC GSGPLEEIYS AGDSLMIRFR TDDTINKKGF
     mtll-2    DFMEAYDGYD SSAPRLGRFC GSGPLEEIYS AGDSLMIRFH TDDTINKKGF
  humtolloid   DYMELFDGYD STAPSLGRYC GSGPPEEVYS AGDSVLVKFH SDDTITKKGF
       htll    DYVELFDGLD STAVGLRFC  GSGPPEEIYS IGDSVLIHFH TDDTINKKGF 1001        1018
     htl1-2    HARYTSTKFQ DALHMKK
     mtll-2    HARYTSTKFQ DALHMRK
  humtolloid   HLRYTSTKFQ DTLHSRK
       htll    HIRYKSIRYP DTTHTKK
```

FIG 1C

SEQUENCE LISTING

```
<160> NUMBER OF SEQ ID NOS: 22

<210> SEQ ID NO 1
<211> LENGTH: 5021
<212> TYPE: DNA
<213> ORGANISM: human
<220> FEATURE:
<221> NAME/KEY: CDS
<222> LOCATION: (365)..(3412)

<400> SEQUENCE: 1
cgcccattgg ctcctcagcc aagcacgtac accaaatgtc tgaacctgcg gttcctctcg      60
tactgagcag gattaccatg gcaacaacac atcatcagta gggtaaaact aacctgtctc     120
acgacggtct aaacccaggc agcctcggcc gccgggcaag tagctccgag cggctgcttc     180
ccggttgcct cgaagaagac aggggcgcc gcgctccgct tgctccgcgc ctgagccatg     240
cccagcagcc ctgtgtaacc accgagtccc ggccggagcc gaccgaccca gtgtgcgccg     300
tctttcggcc gagctgagct ttcgtgcacg caactccctc tgccccagcc ggccccgcgc     360 cacc atg ccc cgg gcg act gca ctt ggg gcc ctg gtg tca ctg ctg ctg    409
     Met Pro Arg Ala Thr Ala Leu Gly Ala Leu Val Ser Leu Leu Leu
      1               5                  10                  15 ctg ctg ccg ctg cct cgc ggc gcc ggg gga ctc ggg gag cgc ccg gac        457
Leu Leu Pro Leu Pro Arg Gly Ala Gly Gly Leu Gly Glu Arg Pro Asp
            20                  25                  30 gcc acc gca gac tac tca gag ctg gac ggc gag gag ggc acg gag cag        505
Ala Thr Ala Asp Tyr Ser Glu Leu Asp Gly Glu Glu Gly Thr Glu Gln
        35                  40                  45 cag ctg gag cat tac cac gac cct tgc aaa gcc gct gtc ttt tgg gga        553
Gln Leu Glu His Tyr His Asp Pro Cys Lys Ala Ala Val Phe Trp Gly
    50                  55                  60 gac att gcc tta gat gaa gat gac ttg aag ctg ttt cac att gac aaa        601
Asp Ile Ala Leu Asp Glu Asp Asp Leu Lys Leu Phe His Ile Asp Lys
65                  70                  75 gcc aga gac tgg acc aag cag aca gtg ggg gca aca gga cac agc aca        649
Ala Arg Asp Trp Thr Lys Gln Thr Val Gly Ala Thr Gly His Ser Thr
 80                  85                  90                  95 ggt ggg ctt gaa gag cag gca tct gag agc agc cca gac acc aca gcc        697
Gly Gly Leu Glu Glu Gln Ala Ser Glu Ser Ser Pro Asp Thr Thr Ala
                100                 105                 110 atg gac act ggc acc aag gaa gct gga aag gat ggc cgg gag aat acc        745
Met Asp Thr Gly Thr Lys Glu Ala Gly Lys Asp Gly Arg Glu Asn Thr
            115                 120                 125 aca ctc ctg cac agc cct ggg acc ttg cat gcc gca gcc aag acc ttc        793
```

```
                                                                -continued

Thr Leu Leu His Ser Pro Gly Thr Leu His Ala Ala Lys Thr Phe
            130                 135                 140 tct ccc cgg gtc cga aga gcc aca acc tca agg aca gag agg ata tgg        841
Ser Pro Arg Val Arg Arg Ala Thr Thr Ser Arg Thr Glu Arg Ile Trp
145                 150                 155 cct gga gga gtc atc ccc tac gtc att gga ggg aac ttc act ggg agc        889
Pro Gly Gly Val Ile Pro Tyr Val Ile Gly Gly Asn Phe Thr Gly Ser
160                 165                 170                 175 cag agg gcc att ttt aag cag gcc atg aga cac tgg gag aag cac acc        937
Gln Arg Ala Ile Phe Lys Gln Ala Met Arg His Trp Glu Lys His Thr
                180                 185                 190 tgt gtg acc ttc ata gaa agg acg gat gag gaa agc ttt att gta ttc        985
Cys Val Thr Phe Ile Glu Arg Thr Asp Glu Glu Ser Phe Ile Val Phe
                195                 200                 205 agt tac aga acc tgt ggc tgt tgc tcc tat gtt ggg cgc cga gga gga       1033
Ser Tyr Arg Thr Cys Gly Cys Cys Ser Tyr Val Gly Arg Arg Gly Gly
                210                 215                 220 ggc cca cag gcc ata tcc att ggg aag aac tgt gac aag ttt ggc att       1081
Gly Pro Gln Ala Ile Ser Ile Gly Lys Asn Cys Asp Lys Phe Gly Ile
225                 230                 235 gtg gct cac gag ctg ggc cat gtg gtt ggg ttt tgg cat gaa cac acc       1129
Val Ala His Glu Leu Gly His Val Val Gly Phe Trp His Glu His Thr
240                 245                 250                 255 cgg cca gac aga gac caa cat gtc acc atc atc agg gaa aac atc cag       1177
Arg Pro Asp Arg Asp Gln His Val Thr Ile Ile Arg Glu Asn Ile Gln
                260                 265                 270 cca ggt cag gag tat aat ttc tta aaa atg gaa gct ggg gaa gtg agc       1225
Pro Gly Gln Glu Tyr Asn Phe Leu Lys Met Glu Ala Gly Glu Val Ser
                275                 280                 285 tct ctg gga gag aca tac gac ttt gac agc atc atg cac tac gcc cgg       1273
Ser Leu Gly Glu Thr Tyr Asp Phe Asp Ser Ile Met His Tyr Ala Arg
        290                 295                 300 aac acc ttc tca aga gga gtt ttc tta gac acc atc ctt ccc cgt caa       1321
Asn Thr Phe Ser Arg Gly Val Phe Leu Asp Thr Ile Leu Pro Arg Gln
        305                 310                 315 gat gac aat ggc gtc agg cca acc att ggc cag cgc gtg cgg ctc agt       1369
Asp Asp Asn Gly Val Arg Pro Thr Ile Gly Gln Arg Val Arg Leu Ser
320                 325                 330                 335 cag gga gac ata gct caa gcc cgg aag ctg tac aaa tgc cca gcg tgt       1417
Gln Gly Asp Ile Ala Gln Ala Arg Lys Leu Tyr Lys Cys Pro Ala Cys
                340                 345                 350 ggg gag acc ctg cag gac aca acg gga aac ttt tct gca cct ggt ttc       1465
Gly Glu Thr Leu Gln Asp Thr Thr Gly Asn Phe Ser Ala Pro Gly Phe
                355                 360                 365 cca aat ggg tac cca tct tac tcc cac tgc gtc tgg agg atc tcg gtc       1513
Pro Asn Gly Tyr Pro Ser Tyr Ser His Cys Val Trp Arg Ile Ser Val
                370                 375                 380 acc cca ggg gaa aag atc gta tta aac ttc aca tcc atg gat ttg ttt       1561
Thr Pro Gly Glu Lys Ile Val Leu Asn Phe Thr Ser Met Asp Leu Phe
385                 390                 395 aaa agc cga ctg tgc tgg tat gat tac gtg gag gtc cgg gat ggt tac       1609
Lys Ser Arg Leu Cys Trp Tyr Asp Tyr Val Glu Val Arg Asp Gly Tyr
400                 405                 410                 415 tgg aga aaa gcc ccc ctt ttg ggc agg ttt tgt ggc gat aag atc ccg       1657
Trp Arg Lys Ala Pro Leu Leu Gly Arg Phe Cys Gly Asp Lys Ile Pro
                420                 425                 430 gag ccc ctc gtc tcc acg gac agc cgg ctc tgg gtg gag ttc cgc agc       1705
Glu Pro Leu Val Ser Thr Asp Ser Arg Leu Trp Val Glu Phe Arg Ser
                435                 440                 445
```

```
agc agc aac atc ttg ggc aag ggc ttc ttt gca gcg tac gaa gct acc   1753
Ser Ser Asn Ile Leu Gly Lys Gly Phe Phe Ala Ala Tyr Glu Ala Thr
            450                 455                 460 tgc ggg gga gac atg aac aaa gat gcc ggt cag att caa tct ccc aac   1801
Cys Gly Gly Asp Met Asn Lys Asp Ala Gly Gln Ile Gln Ser Pro Asn
465                 470                 475 tat ccg gat gac tac aga cct tcc aag gaa tgt gtc tgg agg att acg   1849
Tyr Pro Asp Asp Tyr Arg Pro Ser Lys Glu Cys Val Trp Arg Ile Thr
480                 485                 490                 495 gtt tcg gag ggg ttt cac gtg gga ctt acc ttc caa gct ttt gag att   1897
Val Ser Glu Gly Phe His Val Gly Leu Thr Phe Gln Ala Phe Glu Ile
                500                 505                 510 gaa agg cac gac agc tgt gca tat gac tac ctg gaa gtc cgg gat ggc   1945
Glu Arg His Asp Ser Cys Ala Tyr Asp Tyr Leu Glu Val Arg Asp Gly
            515                 520                 525 ccc acg gaa gag agt gcc ctg atc ggc cac ttt tgt ggc tat gag aag   1993
Pro Thr Glu Glu Ser Ala Leu Ile Gly His Phe Cys Gly Tyr Glu Lys
        530                 535                 540 ccg gag gat gtg aaa tcg agc tcc aac aga ctg tgg atg aag ttt gtg   2041
Pro Glu Asp Val Lys Ser Ser Ser Asn Arg Leu Trp Met Lys Phe Val
545                 550                 555 tcc gat ggc tct atc aat aaa gcg ggc ttt gca gcc aat ttt ttc aag   2089
Ser Asp Gly Ser Ile Asn Lys Ala Gly Phe Ala Ala Asn Phe Phe Lys
560                 565                 570                 575 gag gtg gat gag tgt tcc tgg cca gat cac ggc ggg tgc gaa cat cgc   2137
Glu Val Asp Glu Cys Ser Trp Pro Asp His Gly Gly Cys Glu His Arg
                580                 585                 590 tgt gtg aac acg ctg ggc agc tac aag tgt gcc tgt gac cct ggc tac   2185
Cys Val Asn Thr Leu Gly Ser Tyr Lys Cys Ala Cys Asp Pro Gly Tyr
            595                 600                 605 gag ctg gcc gcc gat aag aag atg tgt gaa gtg gcc tgt ggc ggt ttc   2233
Glu Leu Ala Ala Asp Lys Lys Met Cys Glu Val Ala Cys Gly Gly Phe
        610                 615                 620 att acc aag ctg aat gga acc atc acc agc cct ggg tgg ccg aag gag   2281
Ile Thr Lys Leu Asn Gly Thr Ile Thr Ser Pro Gly Trp Pro Lys Glu
625                 630                 635 tat ccc aca aac aaa aac tgt gtc tgg cag gtg gtg gcc ccc gct cag   2329
Tyr Pro Thr Asn Lys Asn Cys Val Trp Gln Val Val Ala Pro Ala Gln
640                 645                 650                 655 tac cgg atc tcc ctt cag ttt gaa gtg ttt gaa ctg gaa ggc aat gac   2377
Tyr Arg Ile Ser Leu Gln Phe Glu Val Phe Glu Leu Glu Gly Asn Asp
                660                 665                 670 gtc tgt aag tac gac ttt gta gag gtg cgc agc ggc ctg tcc ccc gac   2425
Val Cys Lys Tyr Asp Phe Val Glu Val Arg Ser Gly Leu Ser Pro Asp
            675                 680                 685 gcc aag ctg cac ggc agg ttc tgc ggc tct gag acg ccg gaa gtc atc   2473
Ala Lys Leu His Gly Arg Phe Cys Gly Ser Glu Thr Pro Glu Val Ile
        690                 695                 700 acc tcg cag agc aac aac atg cgc gtg gag ttc aag tcc gac aac acc   2521
Thr Ser Gln Ser Asn Asn Met Arg Val Glu Phe Lys Ser Asp Asn Thr
705                 710                 715 gtc tcc aag cgc ggc ttc agg gcc cac ttc ttc tca gat aag gac gag   2569
Val Ser Lys Arg Gly Phe Arg Ala His Phe Phe Ser Asp Lys Asp Glu
720                 725                 730                 735 tgt gcc aag gac aac ggg ggt tgt cag cat gag tgc gtc aac acc ttc   2617
Cys Ala Lys Asp Asn Gly Gly Cys Gln His Glu Cys Val Asn Thr Phe
                740                 745                 750 ggg agc tac ctg tgc agg tgc aga aac ggc tac tgg ctc cac gag aat   2665
Gly Ser Tyr Leu Cys Arg Cys Arg Asn Gly Tyr Trp Leu His Glu Asn
            755                 760                 765
```

```
ggg cat gac tgc aaa gag gct ggc tgt gca cac aag atc agc agt gtg    2713
Gly His Asp Cys Lys Glu Ala Gly Cys Ala His Lys Ile Ser Ser Val
            770                 775                 780 gag ggg acc ctg gcg agc ccc aac tgg cct gac aaa tac ccc agc cgg    2761
Glu Gly Thr Leu Ala Ser Pro Asn Trp Pro Asp Lys Tyr Pro Ser Arg
        785                 790                 795 agg gag tgt acc tgg aac atc tct tcg act gca ggc cac aga gtg aaa    2809
Arg Glu Cys Thr Trp Asn Ile Ser Ser Thr Ala Gly His Arg Val Lys
800                 805                 810                 815 ctc acc ttt aat gag ttt gag atc gag cag cac cag gaa tgt gcc tat    2857
Leu Thr Phe Asn Glu Phe Glu Ile Glu Gln His Gln Glu Cys Ala Tyr
                820                 825                 830 gac cac ctg gaa atg tat gac ggg ccg gac agc ctg gcc ccc att ctg    2905
Asp His Leu Glu Met Tyr Asp Gly Pro Asp Ser Leu Ala Pro Ile Leu
            835                 840                 845 ggc cgt ttc tgc ggc agc aag aaa cca gac ccc acg gtg gct tcc ggc    2953
Gly Arg Phe Cys Gly Ser Lys Lys Pro Asp Pro Thr Val Ala Ser Gly
        850                 855                 860 agc agt atg ttt ctc agg ttt tat tcg gat gcc tca gtg cag agg aaa    3001
Ser Ser Met Phe Leu Arg Phe Tyr Ser Asp Ala Ser Val Gln Arg Lys
865                 870                 875 ggc ttc cag gca gtg cac agc aca gag tgc ggg ggc agg ctg aag gct    3049
Gly Phe Gln Ala Val His Ser Thr Glu Cys Gly Gly Arg Leu Lys Ala
880                 885                 890                 895 gaa gtg cag acc aaa gag ctc tat tcc cac gcc cag ttt ggg gac aac    3097
Glu Val Gln Thr Lys Glu Leu Tyr Ser His Ala Gln Phe Gly Asp Asn
                900                 905                 910 aac tac ccg agc gag gcc cgc tgt gac tgg gtg atc gtg gca gag gac    3145
Asn Tyr Pro Ser Glu Ala Arg Cys Asp Trp Val Ile Val Ala Glu Asp
            915                 920                 925 ggc tac ggc gtg gag ctg aca ttc cgg acc ttt gag gtt gag gag gag    3193
Gly Tyr Gly Val Glu Leu Thr Phe Arg Thr Phe Glu Val Glu Glu Glu
        930                 935                 940 gcc gac tgc ggc tac gac tac atg gaa gcc tac gac ggc tac gac agc    3241
Ala Asp Cys Gly Tyr Asp Tyr Met Glu Ala Tyr Asp Gly Tyr Asp Ser
945                 950                 955 tca gcg ccc agg ctc ggc cgc ttc tgt ggc tct ggg cca tta gaa gaa    3289
Ser Ala Pro Arg Leu Gly Arg Phe Cys Gly Ser Gly Pro Leu Glu Glu
960                 965                 970                 975 atc tac tct gca ggt gat tcc ctg atg att cga ttc gca aca gat gac    3337
Ile Tyr Ser Ala Gly Asp Ser Leu Met Ile Arg Phe Arg Thr Asp Asp
                980                 985                 990 acc atc aac aag aaa ggc ttt cat gcc cga tac acc agc acc aag ttc    3385
Thr Ile Asn Lys Lys Gly Phe His Ala Arg Tyr Thr Ser Thr Lys Phe
            995                 1000                1005 cag gat gcc ctg cac atg aag aaa tag tgctgatgtt cttgaaagac          3432
Gln Asp Ala Leu His Met Lys Lys
        1010                1015 agaaactgag aattttttttg ttttgttttg ttttaacaa caatagcacc ttgaaaatct  3492
gccctaaaac agtgtacagt atttttctca aacaaaaact cagaatccag ccttagaggt  3552
atatatttga atgaaagtct tgtaagtttg gccaacaagg tggagaaaaa aatgttcttt  3612
tgcttctgtc tgcaatgttg tcattcatga actgttaaag tgttaaagat taggattgga  3672
gtcactgacc attccggcta tgcttcttca taccattctc cttgttgtcc cttgctccta  3732
tgtggcaaaa ggtcagcctt ggggttggcc gttcctctaa tctggacttg cttgcaaagg  3792
tgccaggctg tcttctgtcc atgttgggca taagggatga aaacttggcc gagactaatg  3852
```

-continued

```
tgtgcccac agctttggct ggaatcattt tctttctctc tgccagggac atgtcaacca      3912
agaaacctga aaatatggat ggatgtcagg actaaaaaaa ggcatcacag tgagcagtga      3972
gcacagaggg agtttcgagt ataagaatca ttgtcatgaa gttaggagac acaaagcca      4032 tttctcagag tcattcactc tccttgtccc tttggtttcc ccccttcctt aattgcagtg      4092
ggggctaagg tatccattat gaatacagca gaacatttgc tggcgagagt cctgtctgct      4152
gagaagacaa tattgtggct cgtcctgata tttttcatt cattgacttt gagaagactc      4212
cacctgtgct tggaattcca tgggcttcaa agaacatttc ttcttttagc tttggaggca      4272
cttgccgtgg cacacctgga ctccttgaca tccaattcaa actgcatttg caaaatgtgc      4332
aaagacctct tatgagggac caattcaggt cccttatggg gtgaacactg ttgaagactg      4392
gttaattata agttatgtaa gaatcatcgc cttgtggaac aagtcaatca gtgactagct      4452
tcctgtagcc aatcaggtta agagggcgt tggtaatttt gttctgattt aactagtatt      4512
caatcaccaa cttgcaaaca gaattcataa cacttggcac ttgttctaga gaagtgtaga      4572
ggatgatgtt aacataattt tagcacttca aggtataatt taaacagtga ggtagttttg      4632
aatggcattt cattaaggca tctatgggca ttatgagcta aaagctgtgg tatgttagct      4692
ttaaaagagt atttatgttg gaataatttt taaataatgt ttacataact gtaagtcctg      4752
tttggttgtt gttggacgca gggcggcaca tgagtgtttt tggttagagc caagatagct      4812
cccatgcacc ggaattcctt tgggatgaat cagcatcatt ttaaacaaag tatatgtaaa      4872
aggtgaaagg ttatatttt tacagatcag aatgtggcac cagaggactg tgtctcatta      4932
aagtgattgc tgggagcaaa aactagaatg atacaaagaa aggtcagaga atgcatggg      4992 aatattttt ctttaaaaaa aaaaaaaa                                         5021
```

<210> SEQ ID NO 2
<211> LENGTH: 1015
<212> TYPE: PRT
<213> ORGANISM: human

<400> SEQUENCE: 2

```
Met Pro Arg Ala Thr Ala Leu Gly Ala Leu Val Ser Leu Leu Leu Leu
 1               5                  10                  15

Leu Pro Leu Pro Arg Gly Ala Gly Gly Leu Gly Glu Arg Pro Asp Ala
                20                  25                  30

Thr Ala Asp Tyr Ser Glu Leu Asp Gly Glu Gly Thr Glu Gln Gln
            35                  40                  45

Leu Glu His Tyr His Asp Pro Cys Lys Ala Ala Val Phe Trp Gly Asp
        50                  55                  60

Ile Ala Leu Asp Glu Asp Asp Leu Lys Leu Phe His Ile Asp Lys Ala
    65                  70                  75                  80

Arg Asp Trp Thr Lys Gln Thr Val Gly Ala Thr Gly His Ser Thr Gly
                    85                  90                  95

Gly Leu Glu Glu Gln Ala Ser Glu Ser Ser Pro Asp Thr Thr Ala Met
                100                 105                 110

Asp Thr Gly Thr Lys Glu Ala Gly Lys Asp Gly Arg Glu Asn Thr Thr
            115                 120                 125

Leu Leu His Ser Pro Gly Thr Leu His Ala Ala Ala Lys Thr Phe Ser
        130                 135                 140

Pro Arg Val Arg Arg Ala Thr Thr Ser Arg Thr Glu Arg Ile Trp Pro
145                 150                 155                 160

Gly Gly Val Ile Pro Tyr Val Ile Gly Gly Asn Phe Thr Gly Ser Gln
```

-continued

```
                165                 170                 175
Arg Ala Ile Phe Lys Gln Ala Met Arg His Trp Lys His Thr Cys
                180                 185                 190
Val Thr Phe Ile Glu Arg Thr Asp Glu Glu Ser Phe Ile Val Phe Ser
            195                 200                 205
Tyr Arg Thr Cys Gly Cys Ser Tyr Val Gly Arg Arg Gly Gly Gly
        210                 215                 220
Pro Gln Ala Ile Ser Ile Gly Lys Asn Cys Asp Lys Phe Gly Ile Val
225                 230                 235                 240
Ala His Glu Leu Gly His Val Val Gly Phe Trp His Glu His Thr Arg
                245                 250                 255
Pro Asp Arg Asp Gln His Val Thr Ile Ile Arg Glu Asn Ile Gln Pro
            260                 265                 270
Gly Gln Glu Tyr Asn Phe Leu Lys Met Glu Ala Gly Glu Val Ser Ser
        275                 280                 285
Leu Gly Glu Thr Tyr Asp Phe Asp Ser Ile Met His Tyr Ala Arg Asn
    290                 295                 300
Thr Phe Ser Arg Gly Val Phe Leu Asp Thr Ile Leu Pro Arg Gln Asp
305                 310                 315                 320
Asp Asn Gly Val Arg Pro Thr Ile Gly Gln Arg Val Arg Leu Ser Gln
                325                 330                 335
Gly Asp Ile Ala Gln Ala Arg Lys Leu Tyr Lys Cys Pro Ala Cys Gly
            340                 345                 350
Glu Thr Leu Gln Asp Thr Thr Gly Asn Phe Ser Ala Pro Gly Phe Pro
        355                 360                 365
Asn Gly Tyr Pro Ser Tyr Ser His Cys Val Trp Arg Ile Ser Val Thr
    370                 375                 380
Pro Gly Glu Lys Ile Val Leu Asn Phe Thr Ser Met Asp Leu Phe Lys
385                 390                 395                 400
Ser Arg Leu Cys Trp Tyr Asp Tyr Val Glu Val Arg Asp Gly Tyr Trp
                405                 410                 415
Arg Lys Ala Pro Leu Leu Gly Arg Phe Cys Gly Asp Lys Ile Pro Glu
            420                 425                 430
Pro Leu Val Ser Thr Asp Ser Arg Leu Trp Val Glu Phe Arg Ser Ser
        435                 440                 445
Ser Asn Ile Leu Gly Lys Gly Phe Phe Ala Ala Tyr Glu Ala Thr Cys
    450                 455                 460
Gly Gly Asp Met Asn Lys Asp Ala Gly Gln Ile Gln Ser Pro Asn Tyr
465                 470                 475                 480
Pro Asp Asp Tyr Arg Pro Ser Lys Glu Cys Val Trp Arg Ile Thr Val
                485                 490                 495
Ser Glu Gly Phe His Val Gly Leu Thr Phe Gln Ala Phe Glu Ile Glu
            500                 505                 510
Arg His Asp Ser Cys Ala Tyr Asp Tyr Leu Glu Val Arg Asp Gly Pro
        515                 520                 525
Thr Glu Glu Ser Ala Leu Ile Gly His Phe Cys Gly Tyr Glu Lys Pro
    530                 535                 540
Glu Asp Val Lys Ser Ser Ser Asn Arg Leu Trp Met Lys Phe Val Ser
545                 550                 555                 560
Asp Gly Ser Ile Asn Lys Ala Gly Phe Ala Ala Asn Phe Phe Lys Glu
                565                 570                 575
Val Asp Glu Cys Ser Trp Pro Asp His Gly Gly Cys Glu His Arg Cys
            580                 585                 590
```

```
Val Asn Thr Leu Gly Ser Tyr Lys Cys Ala Cys Asp Pro Gly Tyr Glu
            595                 600                 605

Leu Ala Ala Asp Lys Lys Met Cys Glu Val Ala Cys Gly Gly Phe Ile
            610                 615                 620

Thr Lys Leu Asn Gly Thr Ile Thr Ser Pro Gly Trp Pro Lys Glu Tyr
625                 630                 635                 640

Pro Thr Asn Lys Asn Cys Val Trp Gln Val Ala Pro Ala Gln Tyr
            645                 650                 655

Arg Ile Ser Leu Gln Phe Glu Val Phe Glu Leu Glu Gly Asn Asp Val
            660                 665                 670

Cys Lys Tyr Asp Phe Val Glu Val Arg Ser Gly Leu Ser Pro Asp Ala
            675                 680                 685

Lys Leu His Gly Arg Phe Cys Gly Ser Glu Thr Pro Glu Val Ile Thr
            690                 695                 700

Ser Gln Ser Asn Asn Met Arg Val Glu Phe Lys Ser Asp Asn Thr Val
705                 710                 715                 720

Ser Lys Arg Gly Phe Arg Ala His Phe Phe Ser Asp Lys Asp Glu Cys
                    725                 730                 735

Ala Lys Asp Asn Gly Gly Cys Gln His Glu Cys Val Asn Thr Phe Gly
            740                 745                 750

Ser Tyr Leu Cys Arg Cys Arg Asn Gly Tyr Trp Leu His Glu Asn Gly
            755                 760                 765

His Asp Cys Lys Glu Ala Gly Cys Ala His Lys Ile Ser Ser Val Glu
            770                 775                 780

Gly Thr Leu Ala Ser Pro Asn Trp Pro Asp Lys Tyr Pro Ser Arg Arg
785                 790                 795                 800

Glu Cys Thr Trp Asn Ile Ser Ser Thr Ala Gly His Arg Val Lys Leu
                    805                 810                 815

Thr Phe Asn Glu Phe Glu Ile Glu Gln His Gln Glu Cys Ala Tyr Asp
            820                 825                 830

His Leu Glu Met Tyr Asp Gly Pro Asp Ser Leu Ala Pro Ile Leu Gly
            835                 840                 845

Arg Phe Cys Gly Ser Lys Lys Pro Asp Pro Thr Val Ala Ser Gly Ser
850                 855                 860

Ser Met Phe Leu Arg Phe Tyr Ser Asp Ala Ser Val Gln Arg Lys Gly
865                 870                 875                 880

Phe Gln Ala Val His Ser Thr Glu Cys Gly Gly Arg Leu Lys Ala Glu
                    885                 890                 895

Val Gln Thr Lys Glu Leu Tyr Ser His Ala Gln Phe Gly Asp Asn Asn
            900                 905                 910

Tyr Pro Ser Glu Ala Arg Cys Asp Trp Val Ile Val Ala Glu Asp Gly
            915                 920                 925

Tyr Gly Val Glu Leu Thr Phe Arg Thr Phe Glu Val Glu Glu Ala
            930                 935                 940

Asp Cys Gly Tyr Asp Tyr Met Glu Ala Tyr Asp Gly Tyr Asp Ser Ser
945                 950                 955                 960

Ala Pro Arg Leu Gly Arg Phe Cys Gly Ser Gly Pro Leu Glu Glu Ile
                    965                 970                 975

Tyr Ser Ala Gly Asp Ser Leu Met Ile Arg Phe Arg Thr Asp Asp Thr
            980                 985                 990

Ile Asn Lys Lys Gly Phe His Ala Arg Tyr Thr Ser Thr Lys Phe Gln
            995                 1000                1005
```

-continued

```
Asp Ala Leu His Met Lys Lys
   1010            1015

<210> SEQ ID NO 3
<211> LENGTH: 4661
<212> TYPE: DNA
<213> ORGANISM: mouse
<220> FEATURE:
<221> NAME/KEY: CDS
<222> LOCATION: (191)..(3229)

<400> SEQUENCE: 3
agtcgtgttt agcagcggct tcccgggtgt ccaggccgga cgagaacgcc ttactgggct       60
tgcttggtac cctaccggtg cctggcagcc aagcagcagc caccacaacc gaccctgtac      120
gtggtgtctc tctggatccg agctttctgt gcaggttaag tccctcgggc ccgccgacc      180 ccttgccact atg ccc ctt gcg acc act ctt ggc acc ctg gtg cta ctg        229
            Met Pro Leu Ala Thr Thr Leu Gly Thr Leu Val Leu Leu
              1               5                  10 ttg ctg cta ccg ctg ccc cgc ggt gct gaa gtg act ggg gac cat tcg        277
Leu Leu Leu Pro Leu Pro Arg Gly Ala Glu Val Thr Gly Asp His Ser
 15                  20                  25 aat gtc gcc ttg gac tac gga gcc ttg gaa ggc gag gag ggc acg gag        325
Asn Val Ala Leu Asp Tyr Gly Ala Leu Glu Gly Glu Glu Gly Thr Glu
 30                  35                  40                  45 cag cag ctg cat tac cac gac ccc tgc aaa gct gct gtc ttc tgg gga        373
Gln Gln Leu His Tyr His Asp Pro Cys Lys Ala Ala Val Phe Trp Gly
                 50                  55                  60 gat att gct ctg gat gaa gat gat ctc aag tta ttt cac atc gac aag        421
Asp Ile Ala Leu Asp Glu Asp Asp Leu Lys Leu Phe His Ile Asp Lys
             65                  70                  75 gct gag gac tgg acc aag cca tcc att gac aaa cca gga cat gac act        469
Ala Glu Asp Trp Thr Lys Pro Ser Ile Asp Lys Pro Gly His Asp Thr
         80                  85                  90 gga ggc ctt gag gag aca tct gca agg tgg cca aac gat aca gcc tct        517
Gly Gly Leu Glu Glu Thr Ser Ala Arg Trp Pro Asn Asp Thr Ala Ser
     95                 100                 105 aac gcc agc atc cag gca cca aga aag gat ggc aag gat gcc acc aca        565
Asn Ala Ser Ile Gln Ala Pro Arg Lys Asp Gly Lys Asp Ala Thr Thr
110                 115                 120                 125 ttt ctg cct aac cct ggg acc tca aac acc acc gct aag acc ttc tct        613
Phe Leu Pro Asn Pro Gly Thr Ser Asn Thr Thr Ala Lys Thr Phe Ser
                130                 135                 140 gct cga gtt cga aga gct aca acc tca agg aca gag cgg att tgg cct        661
Ala Arg Val Arg Arg Ala Thr Thr Ser Arg Thr Glu Arg Ile Trp Pro
            145                 150                 155 gga ggg gtc att cct tat gtc att gga gga aac ttt act ggt acc cag        709
Gly Gly Val Ile Pro Tyr Val Ile Gly Gly Asn Phe Thr Gly Thr Gln
        160                 165                 170 agg gcc att ttc aaa cag gcc atg agg cac tgg gag aag cac acc tgt        757
Arg Ala Ile Phe Lys Gln Ala Met Arg His Trp Glu Lys His Thr Cys
    175                 180                 185 gtg acc ttc gta gag agg aca gat gag gaa agc ttc att gta ttc agt        805
Val Thr Phe Val Glu Arg Thr Asp Glu Glu Ser Phe Ile Val Phe Ser
190                 195                 200                 205 tac agg acc tgt ggt tgt tgt tcc tac gtg gga cgc cga gga ggt ggc        853
Tyr Arg Thr Cys Gly Cys Cys Ser Tyr Val Gly Arg Arg Gly Gly Gly
                210                 215                 220 ccg cag gcc ata tcc atc ggg aaa aac tgt gac aag ttc ggc att gtg        901
Pro Gln Ala Ile Ser Ile Gly Lys Asn Cys Asp Lys Phe Gly Ile Val
            225                 230                 235
```

-continued

```
gct cac gag ctg ggc cat gtg gtt ggg ttc tgg cat gaa cac act cgg     949
Ala His Glu Leu Gly His Val Val Gly Phe Trp His Glu His Thr Arg
        240                 245                 250 cca gac cga gac caa cat gtc acc atc atc aga gaa aac atc cag cca     997
Pro Asp Arg Asp Gln His Val Thr Ile Ile Arg Glu Asn Ile Gln Pro
    255                 260                 265 ggt cag gag tat aat ttc tta aaa atg gaa gcc ggc gag gtg agc tct    1045
Gly Gln Glu Tyr Asn Phe Leu Lys Met Glu Ala Gly Glu Val Ser Ser
270                 275                 280                 285 ctg gga gag acc tac gac ttc gac agc atc atg cac tat gcc cgg aac    1093
Leu Gly Glu Thr Tyr Asp Phe Asp Ser Ile Met His Tyr Ala Arg Asn
            290                 295                 300 acc ttc tca aga gga gtt ttc tta gac acc atc ctc ccc cgt cga gac    1141
Thr Phe Ser Arg Gly Val Phe Leu Asp Thr Ile Leu Pro Arg Arg Asp
        305                 310                 315 gac aat ggc gtc agg cca acc att ggc caa cgc gtg cgg ctc agt cag    1189
Asp Asn Gly Val Arg Pro Thr Ile Gly Gln Arg Val Arg Leu Ser Gln
    320                 325                 330 gga gat ata gct caa gcc agg aag ctg tac aaa tgc cca gca tgt ggg    1237
Gly Asp Ile Ala Gln Ala Arg Lys Leu Tyr Lys Cys Pro Ala Cys Gly
335                 340                 345 gag aca cta cag gac acg aca gga aac ttt tcg gca cct ggt ttc cca    1285
Glu Thr Leu Gln Asp Thr Thr Gly Asn Phe Ser Ala Pro Gly Phe Pro
350                 355                 360                 365 aat ggc tac ccc tcc tat tcc cac tgc gtc tgg agg atc tcc gtc acc    1333
Asn Gly Tyr Pro Ser Tyr Ser His Cys Val Trp Arg Ile Ser Val Thr
            370                 375                 380 cca ggg gaa aag atc atc cta aat ttc acc tcc atg gat ttg ttt aag    1381
Pro Gly Glu Lys Ile Ile Leu Asn Phe Thr Ser Met Asp Leu Phe Lys
        385                 390                 395 agc cgc ctg tgc tgg tac gat tac gtg gag atc cgg gat ggt tac tgg    1429
Ser Arg Leu Cys Trp Tyr Asp Tyr Val Glu Ile Arg Asp Gly Tyr Trp
    400                 405                 410 aga aag gcc ccc ctg ttg ggg agg ttc tgt ggc gat aag ata cct gag    1477
Arg Lys Ala Pro Leu Leu Gly Arg Phe Cys Gly Asp Lys Ile Pro Glu
415                 420                 425 tcc ctt gtc tcc tcg gac agc cgg ctc tgg gtg gaa ttc cgt agc agc    1525
Ser Leu Val Ser Ser Asp Ser Arg Leu Trp Val Glu Phe Arg Ser Ser
430                 435                 440                 445 agc agc agc ctg ggc aaa ggc ttc ttt gct gta tat gaa gcc atg tgt    1573
Ser Ser Ser Leu Gly Lys Gly Phe Phe Ala Val Tyr Glu Ala Met Cys
            450                 455                 460 ggg gga gac ata acc aaa gat gca ggc cag att cag tct ccc aac tac    1621
Gly Gly Asp Ile Thr Lys Asp Ala Gly Gln Ile Gln Ser Pro Asn Tyr
        465                 470                 475 cct gac gac tac aga cct tcc aag gaa tgt gtg tgg agg atc aca gtg    1669
Pro Asp Asp Tyr Arg Pro Ser Lys Glu Cys Val Trp Arg Ile Thr Val
    480                 485                 490 ccc gac ggg ttc cat gtg gga ctt acc ttc cag tcc ttc gag atc gaa    1717
Pro Asp Gly Phe His Val Gly Leu Thr Phe Gln Ser Phe Glu Ile Glu
495                 500                 505 agg cat gac agt tgt gca tat gac tat ctg gaa atc cga gac ggt ccc    1765
Arg His Asp Ser Cys Ala Tyr Asp Tyr Leu Glu Ile Arg Asp Gly Pro
510                 515                 520                 525 aca gag gac agc acc ctg att ggc cac ttc tgt ggc tac gag aag ccg    1813
Thr Glu Asp Ser Thr Leu Ile Gly His Phe Cys Gly Tyr Glu Lys Pro
            530                 535                 540 gag gcc gtg aaa tcc agc gct aac cga ctg tgg gtg aag ttt gtg tcc    1861
Glu Ala Val Lys Ser Ser Ala Asn Arg Leu Trp Val Lys Phe Val Ser
```

-continued

|  | 545 |  |  |  | 550 |  |  |  | 555 |  |  |  |
|---|---|---|---|---|---|---|---|---|---|---|---|---|
| gac | ggc | tcc | atc | aat | aaa | gcg | ggc | ttt | gca | gcc | aat | ttc ttc aag gag |
| Asp | Gly | Ser | Ile | Asn | Lys | Ala | Gly | Phe | Ala | Ala | Asn | Phe Phe Lys Glu |
|  |  | 560 |  |  |  | 565 |  |  |  | 570 |  | 1909 |

```
gac ggc tcc atc aat aaa gcg ggc ttt gca gcc aat ttc ttc aag gag    1909
Asp Gly Ser Ile Asn Lys Ala Gly Phe Ala Ala Asn Phe Phe Lys Glu
        560             565             570 gtg gat gag tgc tcc tgg cca gac cat ggt gga tgt gag cag cgc tgt    1957
Val Asp Glu Cys Ser Trp Pro Asp His Gly Gly Cys Glu Gln Arg Cys
575             580             585 gta aac aca ctc ggc agc tac acg tgt gcc tgt gac cct ggc tac gaa    2005
Val Asn Thr Leu Gly Ser Tyr Thr Cys Ala Cys Asp Pro Gly Tyr Glu
590             595             600             605 ctg gct gcc gac aag aag aca tgt gaa gtg gcc tgt ggt ggc ttc att    2053
Leu Ala Ala Asp Lys Lys Thr Cys Glu Val Ala Cys Gly Gly Phe Ile
                610             615             620 acc aag cta aac ggc acc atc acc agc cct gga tgg ccg aag gag tat    2101
Thr Lys Leu Asn Gly Thr Ile Thr Ser Pro Gly Trp Pro Lys Glu Tyr
            625             630             635 ccc acc aac aag aac tgt gtc tgg cag gtg gtg gct ccc gtg cag tac    2149
Pro Thr Asn Lys Asn Cys Val Trp Gln Val Val Ala Pro Val Gln Tyr
        640             645             650 cgc atc tca ctg cag ttc gaa gcc ttt gag ctg gaa ggc aat gac gtc    2197
Arg Ile Ser Leu Gln Phe Glu Ala Phe Glu Leu Glu Gly Asn Asp Val
    655             660             665 tgt aag tat gac ttc gta gag gtg cgc agt ggc ctg tcc cca gat gcc    2245
Cys Lys Tyr Asp Phe Val Glu Val Arg Ser Gly Leu Ser Pro Asp Ala
670             675             680             685 aag ctt cac ggc aaa ttc tgt ggc tcc gag acc ccg gag gtc atc aca    2293
Lys Leu His Gly Lys Phe Cys Gly Ser Glu Thr Pro Glu Val Ile Thr
                690             695             700 tcg cag agc aac aac atg cga gtg gaa ttc aag tct gac aac acc gtc    2341
Ser Gln Ser Asn Asn Met Arg Val Glu Phe Lys Ser Asp Asn Thr Val
            705             710             715 tcc aag cga ggc ttc agg gct cac ttc ttc tca gac aaa gac gag tgt    2389
Ser Lys Arg Gly Phe Arg Ala His Phe Phe Ser Asp Lys Asp Glu Cys
        720             725             730 gcc aaa gac aat ggc ggc tgc cag cag gag tgt gtc aac acg ttc ggg    2437
Ala Lys Asp Asn Gly Gly Cys Gln Gln Glu Cys Val Asn Thr Phe Gly
    735             740             745 agt tac ctg tgc aga tgc agg aac ggg tac cga ctg cat gag aac gga    2485
Ser Tyr Leu Cys Arg Cys Arg Asn Gly Tyr Arg Leu His Glu Asn Gly
750             755             760             765 cac gac tgc aaa gag gct ggc tgc gcc tac aag atc agc agt gca gag    2533
His Asp Cys Lys Glu Ala Gly Cys Ala Tyr Lys Ile Ser Ser Ala Glu
                770             775             780 ggg acc ctg atg agt cct aac tgg cca gac aaa tac ccc agc cgg aag    2581
Gly Thr Leu Met Ser Pro Asn Trp Pro Asp Lys Tyr Pro Ser Arg Lys
            785             790             795 gaa tgt acc tgg aac att tca tca acc gca ggc cac agg gtg aaa att    2629
Glu Cys Thr Trp Asn Ile Ser Ser Thr Ala Gly His Arg Val Lys Ile
        800             805             810 aca ttc agt gag ttc gag att gag cag cac cag gaa tgt gcc tat gac    2677
Thr Phe Ser Glu Phe Glu Ile Glu Gln His Gln Glu Cys Ala Tyr Asp
    815             820             825 cac ctg gaa ctg tac gat ggg aca gac agc ttg gcc ccc atc ctt ggc    2725
His Leu Glu Leu Tyr Asp Gly Thr Asp Ser Leu Ala Pro Ile Leu Gly
830             835             840             845 cgc ttc tgc ggc agc aag aag ccg gat ccc gtg gtg gcg aca ggc agc    2773
Arg Phe Cys Gly Ser Lys Lys Pro Asp Pro Val Val Ala Thr Gly Ser
                850             855             860 agc cta ttc ctc agg ttt tac tcg gac gcc tca gtg cag cgg aaa ggc    2821
```

```
Ser Leu Phe Leu Arg Phe Tyr Ser Asp Ala Ser Val Gln Arg Lys Gly
        865                 870                 875 ttc cag gct gtg cac agc aca gag tgt ggg ggc agg ctg aag gct gaa       2869
Phe Gln Ala Val His Ser Thr Glu Cys Gly Gly Arg Leu Lys Ala Glu
            880                 885                 890 gta cag acc aaa gag ctc tat tcc cat gcc cag ttt ggg gac aac aac       2917
Val Gln Thr Lys Glu Leu Tyr Ser His Ala Gln Phe Gly Asp Asn Asn
        895                 900                 905 tac ccg agc cag gcc cgc tgt gac tgg gtg ata gtg gca gaa gac ggt       2965
Tyr Pro Ser Gln Ala Arg Cys Asp Trp Val Ile Val Ala Glu Asp Gly
910                 915                 920                 925 tat ggc gtg gag ctg ata ttc cgg acc ttt gaa gtt gag gag gaa gct       3013
Tyr Gly Val Glu Leu Ile Phe Arg Thr Phe Glu Val Glu Glu Glu Ala
                930                 935                 940 gac tgt ggc tac gac ttc atg gag gct tat gat ggg tac gac agc tcg       3061
Asp Cys Gly Tyr Asp Phe Met Glu Ala Tyr Asp Gly Tyr Asp Ser Ser
            945                 950                 955 gca ccc agg ctc ggc cgc ttc tgt ggc tca ggg cca tta gag gaa atc       3109
Ala Pro Arg Leu Gly Arg Phe Cys Gly Ser Gly Pro Leu Glu Glu Ile
        960                 965                 970 tac tcc gcc gga gac tcg cta atg atc cgc ttc cac acg gac gac acc       3157
Tyr Ser Ala Gly Asp Ser Leu Met Ile Arg Phe His Thr Asp Asp Thr
975                 980                 985 atc aac aag aaa ggc ttt cac gcc cgg tac act agc acc aag ttc caa       3205
Ile Asn Lys Lys Gly Phe His Ala Arg Tyr Thr Ser Thr Lys Phe Gln
                995                 1000                1005 gac gcc ttg cac atg agg aag tag cgcctcagtt ctggaaaggc agagagactg     3259
Asp Ala Leu His Met Arg Lys
            1010 agggtgtttt aaacacttgc gagtgagcag cctcccatgt acagtgtttt ttctccacaa    3319 caaaaaccca aactatgttc ttgaaactct atatctgggt gacagtacat gcctttggcc    3379 aacgggagga gagagagggg ccgttggttc tggctgtggc gttatcagtc gcagcttctg    3439 gaggaggtca agtttgatg ttagcgacca acaggatga cttcttcaca tttgtctcta     3499 agctttgctc ctgtggctcc gaaggccagc ctggggcaaa aggacagctt agggcaaaag    3559 actgcctctc tctcaactct ggcccggctt ccatagatgg catgagccca gtgtgctggt    3619 gacttggctg ccctctgact actgggcatg gaggattata gattggcagc ggcttcgctg    3679 atactcgcag gtgtggctga acgcttctgt gcagttctac cagagtcaag ccaatcaaga    3739 aaccggagac cgtggacacg agagttaagg tggcatccca gggcacaggg aggggggctca   3799 acctgggaac cacataatgg cgctggaaga ccttgagcat cttcctctgg ccctgcttgt    3859 ccttgtcacc tctggggagc ccctgtcatc agtctccatt cagaaaggag aacccacggt    3919 cactcctagc agaacattcg ctggcgagca ccccaggtt gctgagagga cgcctagctt    3979 cacccaatat ttctcctctg tcagaggct tagaagatga tgtcacctgc gctggggttc    4039 ccagatgtca cctgggctgg ggttcccatg ggcttccagg aacctcccag ctgaaggcac    4099 ctgctctggc gaacctcagc cgctggacag ccagttcaaa cagcatctgc gagacgtgtc    4159 aagtcatctc aggaccaatc cacgtctcac tgggagaaaa ctagtaattc cacattatct    4219 aagagccacc gtctctggaa caaggtggtc tgtggtacga ctcatgtaac cagacaggtt    4279 agagtgcgtg gacggctttg ctgggattaa ccgggaccca gccgccctct tgcactcaga    4339 attctcagca cccctgcact tgctctagcg gcgtgttaag ggtgatgttt acataatttt    4399 agcacctcaa ggtataatcg aaatagtgag gtagttttga atggcatttc gttaaggcat    4459
```

-continued

```
ctctgggcat tatgagctta aaagctgtgg tacgttagct ttctaagagc atttatgttg      4519
gaatactttt aaaataatgt ttacattaac taactgcaag tcctgttggt tgggttggtg      4579
gcaaacgcag ggcggcggca caggagactg ttgctgttag agatggcgta gctcccaagc      4639
accagaatcc ctatgtgatc ta                                               4661
```

<210> SEQ ID NO 4
<211> LENGTH: 1012
<212> TYPE: PRT
<213> ORGANISM: mouse

<400> SEQUENCE: 4

```
Met Pro Leu Ala Thr Thr Leu Gly Thr Leu Val Leu Leu Leu Leu Leu
 1               5                  10                  15

Pro Leu Pro Arg Gly Ala Glu Val Thr Gly Asp His Ser Asn Val Ala
                20                  25                  30

Leu Asp Tyr Gly Ala Leu Glu Gly Glu Gly Thr Glu Gln Gln Leu
            35                  40                  45

His Tyr His Asp Pro Cys Lys Ala Ala Val Phe Trp Gly Asp Ile Ala
        50                  55                  60

Leu Asp Glu Asp Asp Leu Lys Leu Phe His Ile Asp Lys Ala Glu Asp
 65                  70                  75                  80

Trp Thr Lys Pro Ser Ile Asp Lys Pro Gly His Asp Thr Gly Gly Leu
                85                  90                  95

Glu Glu Thr Ser Ala Arg Trp Pro Asn Asp Thr Ala Ser Asn Ala Ser
            100                 105                 110

Ile Gln Ala Pro Arg Lys Asp Gly Lys Asp Ala Thr Thr Phe Leu Pro
        115                 120                 125

Asn Pro Gly Thr Ser Asn Thr Thr Ala Lys Thr Phe Ser Ala Arg Val
130                 135                 140

Arg Arg Ala Thr Thr Ser Arg Thr Glu Arg Ile Trp Pro Gly Gly Val
145                 150                 155                 160

Ile Pro Tyr Val Ile Gly Gly Asn Phe Thr Gly Thr Gln Arg Ala Ile
                165                 170                 175

Phe Lys Gln Ala Met Arg His Trp Glu Lys His Thr Cys Val Thr Phe
            180                 185                 190

Val Glu Arg Thr Asp Glu Glu Ser Phe Ile Val Phe Ser Tyr Arg Thr
        195                 200                 205

Cys Gly Cys Cys Ser Tyr Val Gly Arg Arg Gly Gly Pro Gln Ala
    210                 215                 220

Ile Ser Ile Gly Lys Asn Cys Asp Lys Phe Gly Ile Val Ala His Glu
225                 230                 235                 240

Leu Gly His Val Val Gly Phe Trp His Glu His Thr Arg Pro Asp Arg
                245                 250                 255

Asp Gln His Val Thr Ile Ile Arg Glu Asn Ile Gln Pro Gly Gln Glu
            260                 265                 270

Tyr Asn Phe Leu Lys Met Glu Ala Gly Glu Val Ser Ser Leu Gly Glu
        275                 280                 285

Thr Tyr Asp Phe Asp Ser Ile Met His Tyr Ala Arg Asn Thr Phe Ser
    290                 295                 300

Arg Gly Val Phe Leu Asp Thr Ile Leu Pro Arg Arg Asp Asp Asn Gly
305                 310                 315                 320

Val Arg Pro Thr Ile Gly Gln Arg Val Arg Leu Ser Gln Gly Asp Ile
                325                 330                 335
```

-continued

```
Ala Gln Ala Arg Lys Leu Tyr Lys Cys Pro Ala Cys Gly Glu Thr Leu
        340                 345                 350

Gln Asp Thr Thr Gly Asn Phe Ser Ala Pro Gly Phe Pro Asn Gly Tyr
        355                 360                 365

Pro Ser Tyr Ser His Cys Val Trp Arg Ile Ser Val Thr Pro Gly Glu
        370                 375                 380

Lys Ile Ile Leu Asn Phe Thr Ser Met Asp Leu Phe Lys Ser Arg Leu
385                 390                 395                 400

Cys Trp Tyr Asp Tyr Val Glu Ile Arg Asp Gly Tyr Trp Arg Lys Ala
                405                 410                 415

Pro Leu Leu Gly Arg Phe Cys Gly Asp Lys Ile Pro Glu Ser Leu Val
                420                 425                 430

Ser Ser Asp Ser Arg Leu Trp Val Glu Phe Arg Ser Ser Ser Ser Ser
        435                 440                 445

Leu Gly Lys Gly Phe Phe Ala Val Tyr Glu Ala Met Cys Gly Gly Asp
        450                 455                 460

Ile Thr Lys Asp Ala Gly Gln Ile Gln Ser Pro Asn Tyr Pro Asp Asp
465                 470                 475                 480

Tyr Arg Pro Ser Lys Glu Cys Val Trp Arg Ile Thr Val Pro Asp Gly
                485                 490                 495

Phe His Val Gly Leu Thr Phe Gln Ser Phe Glu Ile Glu Arg His Asp
                500                 505                 510

Ser Cys Ala Tyr Asp Tyr Leu Glu Ile Arg Asp Gly Pro Thr Glu Asp
        515                 520                 525

Ser Thr Leu Ile Gly His Phe Cys Gly Tyr Glu Lys Pro Glu Ala Val
        530                 535                 540

Lys Ser Ser Ala Asn Arg Leu Trp Val Lys Phe Val Ser Asp Gly Ser
545                 550                 555                 560

Ile Asn Lys Ala Gly Phe Ala Ala Asn Phe Phe Lys Glu Val Asp Glu
                565                 570                 575

Cys Ser Trp Pro Asp His Gly Gly Cys Glu Gln Arg Cys Val Asn Thr
                580                 585                 590

Leu Gly Ser Tyr Thr Cys Ala Cys Asp Pro Gly Tyr Glu Leu Ala Ala
        595                 600                 605

Asp Lys Lys Thr Cys Glu Val Ala Cys Gly Gly Phe Ile Thr Lys Leu
        610                 615                 620

Asn Gly Thr Ile Thr Ser Pro Gly Trp Pro Lys Glu Tyr Pro Thr Asn
625                 630                 635                 640

Lys Asn Cys Val Trp Gln Val Val Ala Pro Val Gln Tyr Arg Ile Ser
                645                 650                 655

Leu Gln Phe Glu Ala Phe Glu Leu Glu Gly Asn Asp Val Cys Lys Tyr
                660                 665                 670

Asp Phe Val Glu Val Arg Ser Gly Leu Ser Pro Asp Ala Lys Leu His
        675                 680                 685

Gly Lys Phe Cys Gly Ser Glu Thr Pro Glu Val Ile Thr Ser Gln Ser
        690                 695                 700

Asn Asn Met Arg Val Glu Phe Lys Ser Asp Asn Thr Val Ser Lys Arg
705                 710                 715                 720

Gly Phe Arg Ala His Phe Phe Ser Asp Lys Asp Glu Cys Ala Lys Asp
                725                 730                 735

Asn Gly Gly Cys Gln Gln Glu Cys Val Asn Thr Phe Gly Ser Tyr Leu
                740                 745                 750

Cys Arg Cys Arg Asn Gly Tyr Arg Leu His Glu Asn Gly His Asp Cys
```

-continued

```
            755                 760                 765
Lys Glu Ala Gly Cys Ala Tyr Lys Ile Ser Ser Ala Glu Gly Thr Leu
    770                 775                 780

Met Ser Pro Asn Trp Pro Asp Lys Tyr Pro Ser Arg Lys Glu Cys Thr
785                 790                 795                 800

Trp Asn Ile Ser Ser Thr Ala Gly His Arg Val Lys Ile Thr Phe Ser
                805                 810                 815

Glu Phe Glu Ile Glu Gln His Gln Cys Ala Tyr Asp His Leu Glu
            820                 825                 830

Leu Tyr Asp Gly Thr Asp Ser Leu Ala Pro Ile Leu Gly Arg Phe Cys
        835                 840                 845

Gly Ser Lys Lys Pro Asp Pro Val Val Ala Thr Gly Ser Ser Leu Phe
850                 855                 860

Leu Arg Phe Tyr Ser Asp Ala Ser Val Gln Arg Lys Gly Phe Gln Ala
865                 870                 875                 880

Val His Ser Thr Glu Cys Gly Gly Arg Leu Lys Ala Glu Val Gln Thr
                885                 890                 895

Lys Glu Leu Tyr Ser His Ala Gln Phe Gly Asp Asn Asn Tyr Pro Ser
            900                 905                 910

Gln Ala Arg Cys Asp Trp Val Ile Val Ala Glu Asp Gly Tyr Gly Val
        915                 920                 925

Glu Leu Ile Phe Arg Thr Phe Glu Val Glu Glu Ala Asp Cys Gly
    930                 935                 940

Tyr Asp Phe Met Glu Ala Tyr Asp Gly Tyr Asp Ser Ser Ala Pro Arg
945                 950                 955                 960

Leu Gly Arg Phe Cys Gly Ser Gly Pro Leu Glu Glu Ile Tyr Ser Ala
                965                 970                 975

Gly Asp Ser Leu Met Ile Arg Phe His Thr Asp Thr Ile Asn Lys
            980                 985                 990

Lys Gly Phe His Ala Arg Tyr Thr Ser Thr Lys Phe Gln Asp Ala Leu
        995                 1000                1005

His Met Arg Lys
    1010

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer 1
<221> NAME/KEY: unsure
<222> LOCATION: (12)
<223> OTHER INFORMATION: unsure

<400> SEQUENCE: 5
cargcmatgm gnactgggag                                            20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer 2
<221> NAME/KEY: unsure
<222> LOCATION: (12)
<223> OTHER INFORMATION: unsure

<400> SEQUENCE: 6
```
cargcmatgm gncactggga a                                            21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer 3
<221> NAME/KEY: unsure
<222> LOCATION: (13)
<223> OTHER INFORMATION: unsure

<400> SEQUENCE: 7
gaadgtgttv ckngcrtart gc                                           22

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primer 4

<400> SEQUENCE: 8
tgtggtgtct gggctgctct cagatgc                                      27

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer 5

<400> SEQUENCE: 9
actgtctgct tggtccagtc tctgg                                        25

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primer 6

<400> SEQUENCE: 10
tacctggaag tccgggatgg ccccacg                                      27

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence:
      oligonucleotide primer 7

<400> SEQUENCE: 11
gaggatgtga aatcgagctc caacagac                                     28

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primers 8-11

```
<221> NAME/KEY: unsure
<222> LOCATION: (4)
<223> OTHER INFORMATION: unsure
<221> NAME/KEY: unsure
<222> LOCATION: (13)
<223> OTHER INFORMATION: unsure
<221> NAME/KEY: unsure
<222> LOCATION: (14)
<223> OTHER INFORMATION: unsure
<221> NAME/KEY: unsure
<222> LOCATION: (15)
<223> OTHER INFORMATION: unsure
<221> NAME/KEY: unsure
<222> LOCATION: (19)
<223> OTHER INFORMATION: unsure

<400> SEQUENCE: 12
raanccytty ttnnndatng trtcrtc                                          27

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer 12

<400> SEQUENCE: 13
caacaactac ccgagcgagg cccc                                             24

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:
      oligonucleotide primer 12

<400> SEQUENCE: 14
gaagcctacg acggctacga cagctc                                           26

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer 14

<400> SEQUENCE: 15
gctttcctca tctgtcctct ctacg                                            25

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:
      oligonucleotide primer 15

<400> SEQUENCE: 16
cctgtgtgac cttcgtagag agg                                              23

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:
```

-continued oligonucleotide primer 16

<400> SEQUENCE: 17
tgggagctga gcaatgctaa ctgc                                              24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer 17

<400> SEQUENCE: 18
gaaggtgttc cgggcgtagt gcat                                              24

<210> SEQ ID NO 19
<211> LENGTH: 986
<212> TYPE: PRT
<213> ORGANISM: Homo sapiens

<400> SEQUENCE: 19

```
Met Pro Gly Val Ala Arg Leu Pro Leu Leu Gly Leu Leu Leu Leu
 1               5                  10                  15

Pro Arg Pro Gly Arg Pro Leu Asp Leu Ala Asp Tyr Thr Tyr Asp Leu
                20                  25                  30

Ala Glu Glu Asp Asp Ser Glu Pro Leu Asn Tyr Lys Asp Pro Cys Lys
            35                  40                  45

Ala Ala Ala Phe Leu Gly Asp Ile Ala Leu Asp Glu Glu Asp Leu Arg
        50                  55                  60

Ala Phe Gln Val Gln Gln Ala Val Asp Leu Arg Arg His Thr Ala Arg
    65                  70                  75                  80

Lys Ser Ser Ile Lys Ala Ala Val Pro Gly Asn Thr Ser Thr Pro Ser
                85                  90                  95

Cys Gln Ser Thr Asn Gly Gln Pro Gln Arg Gly Ala Cys Gly Arg Trp
            100                 105                 110

Arg Gly Arg Ser Arg Ser Arg Ala Ala Thr Ser Arg Pro Glu Arg
        115                 120                 125

Val Trp Pro Asp Gly Val Ile Pro Phe Val Ile Gly Gly Asn Phe Thr
    130                 135                 140

Gly Ser Gln Arg Ala Val Phe Arg Gln Ala Met Arg His Trp Glu Lys
145                 150                 155                 160

His Thr Cys Val Thr Phe Leu Glu Arg Thr Asp Glu Asp Ser Tyr Ile
                165                 170                 175

Val Phe Thr Tyr Arg Pro Cys Gly Cys Cys Ser Tyr Val Gly Arg Arg
            180                 185                 190

Gly Gly Gly Pro Gln Ala Ile Ser Ile Gly Lys Asn Cys Asp Lys Phe
        195                 200                 205

Gly Ile Val Val His Glu Leu Gly His Val Val Gly Phe Trp His Glu
    210                 215                 220

His Thr Arg Pro Asp Arg Asp Arg His Val Ser Ile Val Arg Glu Asn
225                 230                 235                 240

Ile Gln Pro Gly Gln Glu Tyr Asn Phe Leu Lys Met Glu Pro Gln Glu
                245                 250                 255

Val Glu Ser Leu Gly Glu Thr Tyr Asp Phe Asp Ser Ile Met His Tyr
            260                 265                 270

Ala Arg Asn Thr Phe Ser Arg Gly Ile Phe Leu Asp Thr Ile Val Pro
```

```
                    275                 280                     285
        Lys Tyr Glu Val Asn Gly Val Lys Pro Pro Ile Gly Gln Arg Thr Arg
            290                 295                 300
        Leu Ser Lys Gly Asp Ile Ala Gln Ala Arg Lys Leu Tyr Lys Cys Pro
        305                 310                 315                 320
        Ala Cys Gly Glu Thr Leu Gln Asp Ser Thr Gly Asn Phe Ser Ser Pro
                        325                 330                 335
        Glu Tyr Pro Asn Gly Tyr Ser Ala His Met His Cys Val Trp Arg Ile
                    340                 345                 350
        Ser Val Thr Pro Gly Glu Lys Ile Ile Leu Asn Phe Thr Ser Leu Asp
                        355                 360                 365
        Leu Tyr Arg Ser Arg Leu Cys Trp Tyr Asp Tyr Val Glu Val Arg Asp
            370                 375                 380
        Gly Phe Trp Arg Lys Ala Pro Leu Arg Gly Arg Phe Cys Gly Ser Lys
        385                 390                 395                 400
        Leu Pro Glu Pro Ile Val Ser Thr Asp Ser Arg Leu Trp Val Glu Phe
                        405                 410                 415
        Arg Ser Ser Asn Trp Val Gly Lys Gly Phe Phe Ala Val Tyr Glu
                    420                 425                 430
        Ala Ile Cys Gly Gly Asp Val Lys Lys Asp Tyr Gly His Ile Gln Ser
                        435                 440                 445
        Pro Asn Tyr Pro Asp Asp Tyr Arg Pro Ser Lys Val Cys Ile Trp Arg
            450                 455                 460
        Ile Gln Val Ser Glu Gly Phe His Val Gly Leu Thr Phe Gln Ser Phe
        465                 470                 475                 480
        Glu Ile Glu Arg His Asp Ser Cys Ala Tyr Asp Tyr Leu Glu Val Arg
                        485                 490                 495
        Asp Gly His Ser Glu Ser Ser Thr Leu Ile Gly Arg Tyr Cys Gly Tyr
                    500                 505                 510
        Glu Lys Pro Asp Asp Ile Lys Ser Thr Ser Ser Arg Leu Trp Leu Lys
                515                 520                 525
        Phe Val Ser Asp Gly Ser Ile Asn Lys Ala Gly Phe Ala Val Asn Phe
            530                 535                 540
        Phe Lys Glu Val Asp Glu Cys Ser Arg Pro Asn Arg Gly Gly Cys Glu
        545                 550                 555                 560
        Gln Arg Cys Leu Asn Thr Leu Gly Ser Tyr Lys Cys Ser Cys Asp Pro
                        565                 570                 575
        Gly Tyr Glu Leu Ala Pro Asp Lys Arg Arg Cys Glu Ala Ala Cys Gly
                    580                 585                 590
        Gly Phe Leu Thr Lys Leu Asn Gly Ser Ile Thr Ser Pro Gly Trp Pro
                595                 600                 605
        Lys Glu Tyr Pro Pro Asn Lys Asn Cys Ile Trp Gln Leu Val Ala Pro
            610                 615                 620
        Thr Gln Tyr Arg Ile Ser Leu Gln Phe Asp Phe Phe Glu Thr Glu Gly
        625                 630                 635                 640
        Asn Asp Val Cys Lys Tyr Asp Phe Val Glu Val Arg Ser Gly Leu Thr
                        645                 650                 655
        Ala Asp Ser Lys Leu His Gly Lys Phe Cys Gly Ser Glu Lys Pro Glu
                    660                 665                 670
        Val Ile Thr Ser Gln Tyr Asn Asn Met Arg Val Glu Phe Lys Ser Asp
                675                 680                 685
        Asn Thr Val Ser Lys Lys Gly Phe Lys Ala His Phe Phe Ser Asp Lys
            690                 695                 700
```

```
Asp Glu Cys Ser Lys Asp Asn Gly Gly Cys Gln Gln Asp Cys Val Asn
705                 710                 715                 720

Thr Phe Gly Ser Tyr Glu Cys Gln Cys Arg Ser Gly Phe Val Leu His
            725                 730                 735

Asp Asn Lys His Asp Cys Lys Glu Ala Gly Cys Asn His Lys Val Thr
        740                 745                 750

Ser Thr Ser Gly Thr Ile Thr Ser Pro Asn Trp Pro Asp Lys Tyr Pro
    755                 760                 765

Ser Lys Lys Glu Cys Thr Trp Ala Ile Ser Ser Thr Pro Gly His Arg
770                 775                 780

Val Lys Leu Thr Phe Met Glu Met Asp Ile Glu Ser Gln Pro Glu Cys
785                 790                 795                 800

Ala Tyr Asp His Leu Glu Val Phe Asp Gly Arg Asp Ala Lys Ala Pro
            805                 810                 815

Val Leu Gly Arg Phe Cys Gly Ser Lys Lys Pro Glu Pro Val Leu Ala
        820                 825                 830

Thr Gly Ser Arg Met Phe Leu Arg Phe Tyr Ser Asp Asn Ser Val Gln
    835                 840                 845

Arg Lys Gly Phe Gln Ala Ser His Ala Thr Glu Cys Gly Gly Gln Val
850                 855                 860

Arg Ala Asp Val Lys Thr Lys Asp Leu Tyr Ser His Ala Gln Phe Gly
865                 870                 875                 880

Asp Asn Asn Tyr Pro Gly Gly Val Asp Cys Glu Trp Val Ile Val Ala
            885                 890                 895

Glu Glu Gly Tyr Gly Val Glu Leu Val Phe Gln Thr Phe Glu Val Glu
        900                 905                 910

Glu Glu Thr Asp Cys Gly Tyr Asp Tyr Met Glu Leu Phe Asp Gly Tyr
    915                 920                 925

Asp Ser Thr Ala Pro Ser Leu Gly Arg Tyr Cys Gly Ser Gly Pro Pro
930                 935                 940

Glu Glu Val Tyr Ser Ala Gly Asp Ser Val Leu Val Lys Phe His Ser
945                 950                 955                 960

Asp Asp Thr Ile Thr Lys Lys Gly Phe His Leu Arg Tyr Thr Ser Thr
            965                 970                 975

Lys Phe Gln Asp Thr Leu His Ser Arg Lys
        980                 985

<210> SEQ ID NO 20
<211> LENGTH: 1013
<212> TYPE: PRT
<213> ORGANISM: Homo sapiens

<400> SEQUENCE: 20

Met Gly Leu Gly Thr Leu Ser Pro Arg Met Leu Val Trp Leu Val Ala
1               5                   10                  15

Ser Gly Ile Val Phe Tyr Gly Glu Leu Trp Val Cys Ala Gly Leu Asp
            20                  25                  30

Tyr Asp Tyr Thr Phe Asp Gly Asn Glu Glu Asp Lys Thr Glu Thr Ile
        35                  40                  45

Asp Tyr Lys Asp Pro Cys Lys Ala Ala Val Phe Trp Gly Asp Ile Ala
    50                  55                  60

Leu Asp Asp Glu Asp Leu Asn Ile Phe Gln Ile Asp Arg Thr Ile Asp
65                  70                  75                  80

Leu Thr Gln Asn Pro Phe Gly Asn Leu Gly His Thr Thr Gly Gly Leu
```

```
                     85                   90                   95
Gly Asp His Ala Met Ser Lys Lys Arg Gly Ala Leu Tyr Gln Leu Ile
               100                 105                 110

Asp Arg Ile Arg Arg Ile Gly Phe Gly Leu Glu Gln Asn Asn Thr Val
           115                 120                 125

Lys Gly Lys Val Pro Leu Gln Phe Ser Gly Gln Asn Glu Lys Asn Arg
       130                 135                 140

Val Pro Arg Ala Ala Thr Ser Arg Thr Glu Arg Ile Trp Pro Gly Gly
145                 150                 155                 160

Val Ile Pro Tyr Val Ile Gly Asn Phe Thr Gly Ser Gln Arg Ala
               165                 170                 175

Met Phe Lys Gln Ala Met Arg His Trp Glu Lys His Thr Cys Val Thr
               180                 185                 190

Phe Ile Glu Arg Ser Asp Glu Ser Tyr Ile Val Phe Thr Tyr Arg
           195                 200                 205

Pro Cys Gly Cys Cys Ser Tyr Val Gly Arg Arg Gly Asn Gly Pro Gln
       210                 215                 220

Ala Ile Ser Ile Gly Lys Asn Cys Asp Lys Phe Gly Ile Val Val His
225                 230                 235                 240

Glu Leu Gly His Val Ile Gly Phe Trp His Glu His Thr Arg Pro Asp
               245                 250                 255

Arg Asp Asn His Val Thr Ile Ile Arg Glu Asn Ile Gln Pro Gly Gln
           260                 265                 270

Glu Tyr Asn Phe Leu Lys Met Glu Pro Gly Glu Val Asn Ser Leu Gly
       275                 280                 285

Glu Arg Tyr Asp Phe Asp Ser Ile Met His Tyr Ala Arg Asn Thr Phe
290                 295                 300

Ser Arg Gly Met Phe Leu Asp Thr Ile Leu Pro Ser Arg Asp Asn
305                 310                 315                 320

Gly Ile Arg Pro Ala Ile Gly Gln Arg Thr Arg Leu Ser Lys Gly Asp
               325                 330                 335

Ile Ala Gln Ala Arg Lys Leu Tyr Arg Cys Pro Ala Cys Gly Glu Thr
           340                 345                 350

Leu Gln Glu Ser Asn Gly Asn Leu Ser Ser Pro Gly Phe Pro Asn Gly
       355                 360                 365

Tyr Pro Ser Tyr Thr His Cys Ile Trp Arg Val Ser Val Thr Pro Gly
       370                 375                 380

Glu Lys Ile Val Leu Asn Phe Thr Thr Met Asp Leu Tyr Lys Ser Ser
385                 390                 395                 400

Leu Cys Trp Tyr Asp Tyr Ile Glu Val Arg Asp Gly Tyr Trp Arg Lys
               405                 410                 415

Ser Pro Leu Leu Gly Arg Phe Cys Gly Asp Lys Leu Pro Glu Val Leu
           420                 425                 430

Thr Ser Thr Asp Ser Arg Met Trp Ile Glu Phe Arg Ser Ser Ser Asn
       435                 440                 445

Trp Val Gly Lys Gly Phe Ala Ala Val Tyr Glu Ala Ile Cys Gly Gly
       450                 455                 460

Glu Ile Arg Lys Asn Glu Gly Gln Ile Gln Ser Pro Asn Tyr Pro Asp
465                 470                 475                 480

Asp Tyr Arg Pro Met Lys Glu Cys Val Trp Lys Ile Thr Val Ser Glu
               485                 490                 495

Ser Tyr His Val Gly Leu Thr Phe Gln Ser Phe Glu Ile Glu Arg His
       500                 505                 510
```

-continued

```
Asp Asn Cys Ala Tyr Asp Tyr Leu Glu Val Arg Asp Gly Thr Ser Glu
        515                 520                 525
Asn Ser Pro Leu Ile Gly Arg Phe Cys Gly Tyr Asp Lys Pro Glu Asp
    530                 535                 540
Ile Arg Ser Thr Ser Asn Thr Leu Trp Met Lys Phe Val Ser Asp Gly
545                 550                 555                 560
Thr Val Asn Lys Ala Gly Phe Ala Ala Asn Phe Phe Lys Glu Glu Asp
                565                 570                 575
Glu Cys Ala Lys Pro Asp Arg Gly Gly Cys Glu Gln Arg Cys Leu Asn
            580                 585                 590
Thr Leu Gly Ser Tyr Gln Cys Ala Cys Glu Pro Gly Tyr Glu Leu Gly
        595                 600                 605
Pro Asp Arg Arg Ser Cys Glu Ala Ala Cys Gly Gly Leu Leu Thr Lys
    610                 615                 620
Leu Asn Gly Thr Ile Thr Thr Pro Gly Trp Pro Lys Glu Tyr Pro Pro
625                 630                 635                 640
Asn Lys Asn Cys Val Trp Gln Val Val Ala Pro Thr Gln Tyr Arg Ile
                645                 650                 655
Ser Val Lys Phe Glu Phe Phe Glu Leu Glu Gly Asn Glu Val Cys Lys
            660                 665                 670
Tyr Asp Tyr Val Glu Ile Trp Ser Gly Leu Ser Ser Glu Ser Lys Leu
        675                 680                 685
His Gly Lys Phe Cys Gly Ala Glu Val Pro Glu Val Ile Thr Ser Gln
    690                 695                 700
Phe Asn Asn Met Arg Ile Glu Phe Lys Ser Asp Asn Thr Val Ser Lys
705                 710                 715                 720
Lys Gly Phe Lys Ala His Phe Phe Ser Asp Lys Asp Glu Cys Ser Lys
                725                 730                 735
Asp Asn Gly Gly Cys Gln His Glu Cys Val Asn Thr Met Gly Ser Tyr
            740                 745                 750
Met Cys Gln Cys Arg Asn Gly Phe Val Leu His Asp Asn Lys His Asp
        755                 760                 765
Cys Lys Glu Ala Glu Cys Glu Gln Lys Ile His Ser Pro Ser Gly Leu
    770                 775                 780
Ile Thr Ser Pro Asn Trp Pro Asp Lys Tyr Pro Ser Arg Lys Glu Cys
785                 790                 795                 800
Thr Trp Glu Ile Ser Ala Thr Pro Gly His Arg Ile Lys Leu Ala Phe
                805                 810                 815
Ser Glu Phe Glu Ile Glu Gln His Gln Glu Cys Ala Tyr Asp His Leu
            820                 825                 830
Glu Val Phe Asp Gly Glu Thr Glu Lys Ser Pro Ile Leu Gly Arg Leu
        835                 840                 845
Cys Gly Asn Lys Ile Pro Asp Pro Leu Val Ala Thr Gly Asn Lys Met
    850                 855                 860
Phe Val Arg Phe Val Ser Asp Ala Ser Val Gln Arg Lys Gly Phe Gln
865                 870                 875                 880
Ala Thr His Ser Thr Glu Cys Gly Gly Arg Leu Lys Ala Glu Ser Lys
                885                 890                 895
Pro Arg Asp Leu Tyr Ser His Ala Gln Phe Gly Asp Asn Asn Tyr Pro
            900                 905                 910
Gly Gln Val Asp Cys Glu Trp Leu Leu Val Ser Glu Arg Gly Ser Arg
        915                 920                 925
```

-continued

```
Leu Glu Leu Ser Phe Gln Thr Phe Glu Val Glu Glu Ala Asp Cys
    930             935             940

Gly Tyr Asp Tyr Val Glu Leu Phe Asp Gly Leu Asp Ser Thr Ala Val
945             950             955             960

Gly Leu Gly Arg Phe Cys Gly Ser Gly Pro Pro Glu Glu Ile Tyr Ser
                965             970             975

Ile Gly Asp Ser Val Leu Ile His Phe His Thr Asp Asp Thr Ile Asn
            980             985             990

Lys Lys Gly Phe His Ile Arg Tyr Lys Ser Ile Arg Tyr Pro Asp Thr
            995             1000            1005

Thr His Thr Lys Lys
    1010

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: conserved
      amino acid residues

<400> SEQUENCE: 21

Ala Met Arg His Trp Glu
 1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: conserved
      amino acid residues

<400> SEQUENCE: 22

His Tyr Ala Arg Asn Thr Phe
 1               5
```

MAMMALIAN TOLLOID-LIKE GENE AND PROTEIN

CROSS-REFERENCE TO RELATED APPLICATIONS

This application claims the benefit of U.S. Provisional Application No. 60/111,873 filed Dec. 11, 1998 and of U.S. Provisional Application No. 60/080,550 filed Apr. 3, 1998. Each application is incorporated herein by reference in its entirety.

STATEMENT REGARDING FEDERALLY SPONSORED RESEARCH OR DEVELOPMENT

To be determined.

BACKGROUND OF THE INVENTION

The present invention relates to the field of bone morphogenetic proteins and more particularly to genes and proteins in the BMP-1/Tld family.

Bone formation in mammals such as mice and humans is governed by a set of bone morphogenetic proteins (BMP). Of the seven BMPs known to participate in osteogenesis, six (designated BMP-2 through BMP-7) belong to the TGF-β super family. The seventh BMP (designated BMP-1) is not TGF-β-like, but instead appears to derive from a different gene family. The BMP-1 gene family members typically contain the following domains: an astacin-like metalloprotease domain, one or more EGF-like motifs which in other proteins are thought to bind $Ca^{++}$, and a number of CUB domains. A CUB domain is a motif that mediates protein-protein interactions in complement components C1r/C1s which has also been identified in various proteins involved in developmental processes. BMP-1 was described, at the nucleotide sequence level, by Wozney, J. M., et al., *Science* 242:1528–1534 (1988).

The mammalian BMP-1 domain structure is shared by proteins found in other non-mammalian species. These proteins include *Drosophila tolloid* (Tld) (Shimell, M. J., *Cell* 67:469–481 (1991)), a tolloid-like *Drosophila* gene product (Tlr-1 or tolkin) (Nguyen, T., *Dev. Biol.* 166:569–586 (1994) and Finelli, A. L., et al., *Genetics* 141:271–281 (1995)), a sea urchin BMP-1 homolog (suBMP-1) (Hwang, S. P., et al., *Development* 120:559–568 (1994)), two related sea urchin developmental gene products, SpAN and BP10 (Reynolds, S. D., et al., *Development* 114:769–786 (1992) and Lepage, T., et al., *Development* 114:147–164 (1992)), a Xenopus BMP-1 (xBMP-1) (Maeno, M. et al., *Gene* 134:257–261 (1993), a *Xenopus tolloid* (Lin. J., et al., *Develop. Growth Differ.* 39:43–51 (1997), a tolloid-like Xenopus gene product named xolloid (Piccolo, S. et al., *Cell* 91:407–416 (1997), a related member of the family isolated from zebrafish and called zebrafish tolloid (Bladder, P. et al., Science 278:1937–1940 (1997), a mammalian tolloid (mTld) (Takahara, K. et al., *J. Biol. Chem.* 269:32572–32578 (1994)) and a mammalian tolloid-like gene (mTll-1) (Takahara, K. et al., *Genomics* 34:157–165 (1996)). Some of the nucleic acid sequences of the genes that encode these proteins are known. The mammalian BMP1 gene encodes both the BMP-1 protein and the mTld protein, albeit on two distinct, alternately spliced mRNA molecules. The papers mentioned in this paragraph are incorporated herein by reference.

BRIEF SUMMARY OF THE INVENTION

The present invention is summarized in that a novel mammalian tolloid-like gene product (mTll-2) and its cognate polynucleotide gene, mTLL-2, are distinct from mTld and from all other known BMP-1-related gene products and their cognate polynucleotides, including mTll (now designated mTll-1). The human and murine versions of the gene are reported herein as SEQ ID NO:1 and SEQ ID NO:3, respectively. The amino acid sequences encoded by each are presented as SEQ ID NO:2 and SEQ ID NO:4, respectively.

It is an object of the present invention to provide a gene and gene product involved in the deposition of extracellular matrix in vertebrates (e.g., in osteogenesis).

It is another object of the present invention to provide a target molecule for rational development of a drug for inhibiting activity of the tolloid-like genes to treat fibrosis, scarring, keloids, surgical adhesions, and the like.

It is yet another object of the present invention to provide a recombinant DNA construct, and a protein encoded by the construct, for use in accelerated wound and fracture healing.

It is still another object of the present invention to provide markers that map to the 10q24 region of human chromosome 10 and to the distal end of chromosome 19 in mice.

It is still another object of the present invention to provide nucleotide sequences that function as probes for a non-BMP-1 bone morphogenetic protein gene in mammalian cells.

Other objects, features, and advantages of the present invention will become apparent upon consideration of the following detailed description considered in conjunction with the accompanying drawings.

BRIEF DESCRIPTION OF THE SEVERAL VIEWS OF THE DRAWINGS

FIG. 1A–1C (together, "FIG. 1") aligns the deduced amino acid sequences of the disclosed mTll-2 human (htll-2; SEQ ID NO:1) and murine (mtll-2; SEQ ID NO:3) genes to those of the human mTld (humtolloid; SEQ ID NO:19) and human mTll-1 (htll; SEQ ID NO:20) genes. Alignment was performed using the PileUp program (Genetics Computer Group, Madison, Wis.), with a GAP weight of 12 and GAP length weight of 4. The approximate endpoints of the protein domains are as indicated in provisional application serial No. 60/080,550, incorporated herein by reference.

DETAILED DESCRIPTION OF THE INVENTION

Mammalian tolloid-like 2 (mTll-2) is a genetically distinct member of the subfamily of astacin-like proteases of which bone morphogenetic protein-1 (BMP-1) is the prototype. This subfamily of proteases, which also includes mammalian tolloid (mTld) and mammalian tolloid-like 1 (mTll-1; formerly referred to as mTll), represents key control points in developmental and homeostatic processes, in wound healing, and in pathological processes such as fibrosis. The gene encoding mTll-2 has spatial and temporal expression profiles that differ from the other members of the BMP-1 family and is expressed in soft tissues at highest levels in adult and developing heart as ascertained by means of northern and master blots (Clontech) of RNA from developing and adult human and mouse tissues. The mTll-2 genes exemplified herein are particularly distinguishable from other members of the BMP-1 family of genes at the 3' end of the coding sequence (which encodes the carboxy terminal 17 amino acids of the mTll-2 proteins) and in the section that encodes the proregion of the proteins. The proteins are similarly distinguishable from other proteins in the family.

The inventors have determined that, unlike BMP-1, mtld and mTll-1, mTll-2 is not a procollagen C-proteinase and does not cleave chordin. mTll-2 weakly cleaves prolysyl oxidase to mature active forms. The protein may also cleave other substrates involved in matrix deposition, development, homeostasis, wound healing and disease. The mTll-2 protein will likely optimally cleave a subset of substrates different from those for which BMP-1, mTld and mtll-1 are optimal, despite some overlaps in substrate specificity with those proteins. mTll-2 is a potential target for anti-fibrotic drugs, may accelerate healing in various tissues, and is also useful for studying developmental and disease processes and for identifying its functional inhibitors. Inhibition of mTll-2 may inhibit fibrosis, excess scarring, or other derangements of normal healing or development. Use of recombinant mTll-2 (or its cognate nucleic acids) may be of use in systems for evaluating development, disease processes, and therapeutic intervention.

The mTll-2 protein may act by activating growth factors and morphogens. As such, it may accelerate healing if added exogenously (or if cognate nucleic acids are added into cells, for example, in a genetic therapy).

Polynucleotides (e.g., genomic DNA, messenger RNA, and cDNA corresponding to messenger RNA) that encode mTll-2 can be amplified under suitable amplification conditions from a template library that comprises mammalian polynucleotides, using primers that correspond to conserved regions of the catalytic domains of previously reported astacin metalloproteases. The following degenerate oligonucleotide primers (shown using standard IUPAC nomenclature) are suitable for obtaining a portion of the mTll-2 gene, and are considered preferred by the inventors:

```
Primer 1 (forward):
5'-CARGCMATGMGNCACTGGGAG-3'  (SEQ ID NO:5)

Primer 2 (forward):
5'-CARGCMATGMGNCACTGGGAA-3'  (SEQ ID NO:6)

Primer 3 (reverse)
5'-GAADGTGTTVCKNGCRTARTGC-3' (SEQ ID NO:7)
```

A suitable template library comprising mammalian polynucleotides is preferably a pool of unamplified cDNAs from human placenta or from mouse embryos 7 days post coitum. The cDNAs in the pool are preferably prepared by RT-PCR amplification of mRNAs. Suitable human and mouse placental and embryo cDNA pools are commercially available from Clontech. The source of the template cDNA is not critical, as long as the cDNA pool includes at least one template sequence that can be amplified as described. Other suitable templates can include, but are not limited to, an organ-specific or other type of cDNA pools or libraries or genomic DNA or library.

Suitable amplification conditions are detailed in the Examples below, although one skilled in the art can determine acceptable conditions that differ from those reported herein. Once the initial PCR product is obtained, it can be used for plate screening of cDNA or genomic libraries.

It may be necessary to separately establish the 5' or 3' end of the cDNA sequences encoding mTll-2 using, for example, a method that selectively amplifies only 5' or 3' end cDNA sequences, such as 3'-degenerate PCR or Rapid Amplification of cDNA Ends ("RACE"), Frohman, M. A. "Rapid amplification of complementary DNA ends for generation of full-length complementary DNAs: Thermal RACE" in *Methods in Enzymology* (Wu, R., ed.) Vol. 218, pp. 340–362, Academic Press, New York (1991), incorporated herein by reference in its entirety.

A commercial system for 5' and 3' RACE amplification is available from Clontech. Suitable primers for 5' and 3' RACE can be deduced from sequences of amplified cDNAs obtained during the initial PCR with degenerate primers described above or from sequences of cDNA clones obtained by screening cDNA or genomic DNA libraries. In the preferred embodiment, primers for nested PCR, designed according to the 5' end of a 1.6 kb cDNA isolated from the plate screening, were:

```
Primer 4
5'-TGTGGTGTCTGGGCTGCTCTCAGATGC-3'   (SEQ ID NO:8)

Primer 5
5'-ACTGTCTGCTTGGTCCAGTCTCTGG-3'    (SEQ ID NO:9).
```

For 3'-degenerate PCR, suitable nested primers correspond to sequences at the 3' end of a cDNA isolated from plate screening and a suitable degenerate primer corresponds to a conserved sequence found in BMP-1/tolloid-like proteins in CUB domain 5. Suitable primers include:

```
Primer 6
5'-TACCTGGAAGTCCGGGATGGCCCCACG-3'   (SEQ ID NO:10)

Primer 7
5'-GAGGATGTGAAATCGAGCTCCAACAGAC-3'  (SEQ ID NO:11)

Primers 8–11 (degenerate primer)
5'-RAANCCYTTYTTNNNDATNGTRTCRTC-3'   (SEQ ID NO:12)
```

For 3' RACE, suitable nested PCR primers corresponding to the sequences at the 3' end of the cDNA fragment amplified using 3'-degenerate PCR are:

```
Primer 12
5'-CAACAACTACCCGAGCGAGGCCCC-3'   (SEQ ID NO:13)

Primer 13
5'-GAAGCCTACGACGGCTACGACAGCTC-3'  (SEQ ID NO:14).
```

One of ordinary skill in the art can join the separate cloned sequences together, as the inventors have done, to produce the complete full-length cDNA obtained from a human, as shown in SEQ ID NO:1. Presented herein in SEQ ID NO:1 is an open reading frame flanked by 5'- and 3'-untranslated sequences. The open reading frame encodes a mammalian tolloid-like protein termed mTll-2. The human mTll-2 gene maps to human chromosome 10q24.

A second mTll-2 gene, obtained from a murine source, is shown in SEQ ID NO:3. A corresponding protein encoded by the murine mTll-2 gene is reported at SEQ ID NO:4. The murine version corresponds to the human mTll-2 gene in that the two share similar nucleic acid and amino acid sequences. The murine mTll-2 gene has not yet been mapped to a region of the murine chromosome.

A preparation of polynucleotide (e.g., DNA) molecules containing an mTll-2 gene sequence from any source is considered substantially pure if more than 90% of any cellular material of any host cell in which the DNA has resided has been removed from the DNA preparation. Cellular material can be removed from a nucleic acid preparation, for example, by using a commercial purification kit such as is available from Qiagen (Chatsworth, Calif.). It is preferred that greater than 10% of the nucleic acid molecules in a nucleic acid preparation comprise the complete or partial mTll-2 gene. More preferably, greater than 50%, and yet more preferably, greater than 90%, of the nucleic acid molecules comprise the complete or partial sequence.

In view of the similarity to other tolloid-like proteins, it is expected that the product encoded by the disclosed mTll-2 gene will have a key role in development and in homeostatic processes such as wound healing. The protein is involved in maturation of extracellular matrix precursors into macromolecular structures, e.g., by activating prolysyl oxidase. The protein may also have a role in activation of growth factors in vivo and in vitro, and may accelerate developmental and homeostatic processes when an effective amount of the protein is administered to a tissue. On the other hand, if the mTll-2 protein function is inhibited, such processes may themselves be inhibited, which property can be exploited advantageously upon delivery of an effective amount of an inhibitor to prevent fibrosis and excess scarring or other abnormalities of wound healing. An effective amount of the protein to be delivered to a target site for activating developmental and homeostatic properties can readily be determined by testing a range of amounts of the protein on a selected veterinary species or on a model species having acknowledged biochemical or physiological similarity to humans. In the case of skin or heart wound healing or development, for example, porcine skin or heart is a suitable model for human skin or heart. Rat or rabbit heart are also acceptable systems.

Likewise, an effective amount of an inhibitor of the mTll-2 protein can also be determined. An effective amount is an amount effective upon administration that reduces the occurrence of fibrosis, scarring or keloids compared to an untreated animal, where the assessment of such conditions is made according to accepted clinical or veterinary standards. Such a test is preferably performed in a model system generally accepted as having relevance to human skin, heart or other affected tissue.

The ability to work with proteins of the BMP system has been hampered by the fact that the proteins are typically present in very small amounts in animal tissues. mTll-2, a previously unknown gene, can be cloned into a suitable expression vector containing a transcriptional promoter effective in a suitable mammalian or insect host cell, introduced into and expressed in the suitable host cells, and purified in a native configuration, all using conventional methods. The cDNA can be inserted into an integratable (e.g., a pCDNA3.1-type) or episomal (e.g., a pCEP4-type) vector and expressed in suitable cultured mammalian cells (e.g., 293 human embryonic kidney cells or 293-EBNA cells, respectively). The pCDNA3.1 and pCEP4 vectors (and related vectors) are commercially available from Invitrogen. Vector sequences and restriction maps of the vectors are also available from Invitrogen. The cDNA can also be inserted into a baculovirus vector (e.g., BacPAK 6, commercially available from Clontech).

The protein thus expressed can remain inside the host cell or can be secreted to the extracellular growth medium, if a suitable signal sequence is provided on the construct. The protein can be purified from the cell or from the growth medium by conventional methods. The recombinant protein (and its cognate mRNA) can be used for functional assays and for high throughput screening of inhibitors. The recombinant protein and portions of the protein can be produced from subclones of the sequences disclosed herein and can be used for x-ray crystallography for rational drug design. Antibodies specific to the mTll-2 protein can be designed.

Suitable promoters of transcription include cyotomegalogvirus immediate early promoter such as is found in the pCDNA3.1 or pCEP vectors, or the baculovirus very late promoter found on vector pFASTBac1, which vector is commercially available from Gibco-BRL. Another suitable promoter is baculovirus immediate early promoter such as is found on the pAcPIE1 vector (Novagen, Madison, Wis.). Any other advantageous expression elements such as enhancers, terminators, and the like, as are known to the art, can be included on the suitable expression vector.

A suitable host would be insect tissue culture cells, such as cell line Sf21, Sf9, High Five (Invitrogen, San Diego, Calif.), or mammalian 293 or 293-EBNA cells.

Suitable portions of the gene comprising less than the full coding sequence can also be advantageously cloned into the suitable expression vector to form a recombinant genetic construct. It is understood that a construct prepared in accordance with the invention, need not necessarily contain the entire mTll-2 locus or coding region, but could contain one or more portions thereof encoding a desired function, or containing a portion of the gene having other useful properties, for example, complementarity to a desired genomic sequence. It is understood by those of ordinary skill that certain variation in the size or sequence of the mTll-2 protein (and in the corresponding genetic material encoding the mTll-2 protein) will not interfere with the functions thereof. Such modified forms can be engineered using known methods that may be advantageously employed when constructing genetic constructs containing the complete or partial mTll-2 gene, and in proteins encoded thereby.

Such changes, modifications, additions and deletions are contemplated to fall within the scope of the present invention, as long as the protein retains a desired function known to be associated with the protein. The protein is competent if it retains an ability to cleave, e.g., prolysyl oxidase, in a standard assay for such cleavage. One of ordinary skill is familiar with the necessary controls that should accompany any such assay. It may, alternatively, be desired that the protein lose a certain function as a result of such a change, and such a situation is also envisioned to be within the scope of the present invention.

A substantially pure preparation of the protein thus produced is defined as a preparation wherein the characteristic activity of the mTll-2 protein (such as weak cleavage of prolysyl oxidase) is not affected by the presence of other proteins or molecules in the preparation. Depending upon the use to which the protein will be put, it may be that the mTll-2 protein accounts for at least 10%, preferably at least 50%, more preferably at least 75%, and most preferably at least 95% of the protein in the substantially pure protein preparation. The protein preparation can be enhanced for the protein of interest by labeling the protein with an affinity tag and passing the preparation over a column having an affinity for the tag. It is also possible to employ a processing tag such that a properly processed form of the protein (lacking the cleaved proregion) can be eluted from a column loaded with a crude preparation.

When the murine mTll-2 protein sequence is compared to other tolloid-like genes, no extensive homology exists between it and the proregion of either of the two mammalian proteins (mTld and mTll) or the proregion of either of the two Drosophila proteins (Tld or Tlr-1). FIG. 1 aligns the amino acid sequences of the disclosed human and murine mTll-2 genes to those of the human mTld and human mTll-1 genes. Alignment was performed using the PileUp program (Genetics Computer Group, Madison, Wis.), with a GAP weight of 12 and GAP length weight of 4. FIG. 1 also notes the approximate boundaries of the various domains of the proteins encoded by the indicated coding sequences. The amino acid sequences presented in FIG. 1 are, from top to bottom, human mTll-2, mouse mTll-2, mTld, and mTll-1, respectively.

The mTll-2 mRNA transcript appears not to be alternatively spliced since only a single transcript was detected and because only a single type of mTll-2 cDNA was isolated during cDNA library screenings and PCR amplifications in each species.

Relatively strong mTll-2 mRNA expression was observed in placenta and heart.

It is specifically envisioned that equivalents of the mTll-2 gene can be isolated from other species, by probing a cDNA library from cells of an appropriate species with a probe selected to include an mTll-2-specific portion of the described mouse gene or by PCR amplification with degenerate primers similar to, or differing from, those described above. An mTll-2-specific portion of the mouse mTll-2 gene can be obtained by comparing the nucleic acid sequence of the mouse mTll-2 coding region to that of BMP-1/mTld and mTll-1 and selecting a portion of the mTll-2 gene that has no equivalent in either gene. To be an effective probe, the selected sequence should not contain repeat sequences that would cross-hybridize to numerous genomic sites. The probe should be at least about 200 bases long. It is recognized that the genes of the BMP-1 family are most variable in the regions that encode the proregion and the C-terminal 17 amino acids of the proteins, and it is anticipated that suitable probes can be isolated from those regions of the mTll-2 gene. Such a probe fragment can be converted into a probe by nick translation, end labeling, or other suitable technique known to the art. It is also understood that a desired fragment (or indeed an entire gene) can be synthesized in vitro using well-known techniques available to the molecular biologist. One skilled in the art can design degenerate primers that correspond to regions either unique to mTll-2 or conserved among members of the BMP-1/mTll-1/mTll-2 family of proteins.

Because defects in mTll-2 may lead to genetic abnormalities in people, the chromosomal position (10q24) of the human TLL-2 gene was established as described below in the Examples. This location is near the map position associated with a human genetic condition, spastic paraparesis with amyotrophy. The TLL-2 gene was independently mapped by fluorescence in situ hybridization (FISH) on human metaphase chromosome spreads by the method of Trask, B., *Methods Cell Biol.* 35: 1–35 (1992) and by radiation hybrid screening.

It should also be possible to use PCR to amplify a portion of a genome that corresponds to the mTll-2 region, by selecting specific primers expected to flank the mTll-2 gene (or any portion of the gene). Two mTll-2-specific portions of the gene can serve as suitable primers. It may not be effective to select primers outside the coding portion of the gene because reduced selective pressure on non-coding portions results in greater divergence between mice and humans and other species in those regions. It is specifically noted that the genes of the BMP family from humans and model species such as the mouse are particularly sought after for their relation to human deformities (see, e.g., "The Chicken With a Duck's Feet: It's All in the Biochemical Signal," *The New York Times,* National Edition, p. B6 (May 21, 1996)).

It is also specifically envisioned that large quantities of the protein encoded by the mTll-2 gene can be expressed in (or secreted from) host cells, purified to a substantially pure preparation and used in subsequent functional assays. In one such functional assay, functional attributes of the expressed protein will be described. The protein functions are expected to include a metalloprotease activity, and prolysyl oxidase processing activity, and an activating activity for TGF-β-like proteins, such predictions being reasonable in view of the gross structural similarity to known proteins at the domain level.

In another assay, the protein can be used to screen putative agents having inhibitory activity against the protein. Given that mTll-2 may be able to rescue BMP-1 knockout mice, it will be important for any therapeutic system that modifies or eliminates BMP-1 protein function to similarly alter the mTll-2 protein function. Thus, any panel of such agents must be screened against mTll-2 protein. In such an assay, all components of an assay that support mTll-2 function can be added together, under suitable conditions of salt and pH, and combined with a panel of putative inhibitors of protein function. Using established assays of protein function (described in documents incorporated elsewhere herein by reference), it will be possible to determine whether any tested agent can inhibit protein activity, thereby making it a likely candidate for use in a therapeutic amount to inhibit fibrosis, or to reduce scarring, or reduce keloids. Such screening efforts are underway using related proteins from the BMP-1 family of genes.

It is now also possible to embark upon a rational drug design strategy using the disclosed protein or fragments thereof. In doing so, the protein or fragments will be subjected to x-ray crystallographic analysis to determine their active sites and sites that are available for interaction with a putative therapeutic agent.

The protein encoded by BMP-1 was recently shown to cleave procollagen near the C-terminus. This C-proteinase activity, which is essential to the production of collagen, had long been thought to reside in a protein that had remained elusive. There is great commercial interest in harnessing the C-proteinase activity as a therapeutic agent in collagen-related diseases. It is specifically contemplated that parts of the protein encoded by mTll-2 can be used in an effort to produce an alternative C-proteinase and, both by incorporating the gene into a recombinant vector for ex vivo production of therapeutic protein, and for direct administration in a genetic therapy. The human gene has particular utility for these applications.

The invention will be better understood upon consideration of the following non-limiting Examples.

EXAMPLES

Human mTll-2 From Human Placental cDNA

PCR amplification using degenerate primers. A portion of an mTll-2 gene was amplified from a human placental Marathon-Ready eDNA library (Clontech) using degenerate primers that corresponded to a pair of regions that are conserved in catalytic domains of BMP-1/tolloid-like astacin metalloproteases (see Bond, J. S. and R. J. Benyon, *Protein Science* 4:1247–1261 at 1249 (1995), incorporated herein by reference). To determine a suitable sequence for the degenerate primers, the corresponding nucleotide sequences of human (Wozney et al., 1988), mouse (Fukagawa et al., 1994) and Xenopus (Ma__no et al., 1993) BMP-1; Drosophila tolloid-related-1 (Nguyen et al., 1994); and mouse (Takahara et al., 1996) and human mTll-1 were manually aligned. A pair of 5' (forward) oligonucleotide primers denoted Primer 1:5'-CARGCMATGMGNCACTGGGAG-3' (SEQ ID NO:5) and Primer 2:5'-CARGCMATGMGNCACTGGGAA-3'(SEQ ID NO:6) corresponds to a sequence that encodes the more amino-terminal amino acid conserved residues AMRHWE (SEQ ID NO:21). The two forward primers differ only at the most 3' base corresponding to the wobble position of a codon for E. A 3' (reverse) oligonucleotide primer denoted Primer 3:5'-GAADGTGTTVCKNGCRTARTGC-3' (SEQ ID NO:7) corresponded to a sequence that encodes the more carboxy-terminal amino acid conserved residues HYARNTF (SEQ ID NO:22).

The PCR was performed with denaturation at 95° C./5 min, followed by 30 cycles of 95° C./45 s, 50° C./45 s, 72° C./2 min, and final extension at 72° C./10 min, using 0.5 ng of the human placenta cDNA as template.

A heterogeneous 375 bp PCR product observed upon electrophoresis was excised from a 2% agarose gel and was then ligated into the commercially available pCR 2.1 vector (Invitrogen), the nucleic acid sequence of which is published. The ligation reaction was restricted with ApaI, which cleaves within BMP-1/mTld sequences, to reduce the background of BMP-1/mTld clones. Sequence analysis of clones revealed a PCR product of about 375 bp obtained using primer 2 in combination with primer 3. No mTll-2 or other novel (eg. non-BMP-1/mTld or mTll-1) products were obtained using primer 1 in combination with primer 3. The human mTll-2 sequences reported herein were confirmed by sequencing both strands.

cDNA Library Screening. The 375 bp human mTll-2 PCR fragment was radiolabeled with $^{32}$P-dCTP (Amersham) by random priming (Feinberg, A. P., and Vogelstein, B. (1983). A technique for radiolabeling DNA restriction endonuclease fragments to high specific activity. *Anal. Biochem.* 132:6–13, incorporated herein by reference in its entirety) and was used to screen plaques of a gt11 human placenta cDNA library (Clontech). Hybridization was at 65° C. for 18 h with washing in 2×SSC, 0.1% SDS for 30 min at room temperature; in 2×SSC, 0.1% SDS for 30 min at 65° C.; and in 0.1×SSC, 0.1% SDS for 30 min at 65° C.

One strongly hybridizing positive was plaque purified and an insert of about 1.6 kb (corresponding approximately to the proregion, catalytic, CUB1, and CUB2 domains typical of genes in the BMP-1 family) was excised, subcloned into the EcoRI site of pBluescript II KS$^+$ and sequences were obtained from double-stranded templates by dideoxy chain termination, as described in Lee S. T., et al., "Construction of a full-length cDNA encoding human pro-alpha 2(I) collagen and its expression in pro-alpha 2(I)-deficient W8 rat cells," *J. Biol. Chem.* 263:13414–13418 (1988), incorporated herein by reference in its entirety.

Ends of subclones were sequenced using T3 and T7 primers with internal portions of subclones made accessible to sequencing by introducing deletions or using primers complementary to insert sequences. Further attempts at plate screening failed to generate additional positive clones encoding novel mTll-2 sequences.

RACE-PCR and PCR with degenerate primers for completing the 5' and 3' ends of human mTll-2 cDNA sequences. To obtain all sequences between the 1.6 kb fragment (obtained as described above) and the mTll-2 cDNA 5' end sequences, 5' RACE PCR amplification of 0.5 ng of human placenta Marathon-Ready cDNA template was performed using the Marathon cDNA Amplification Kit, using the manufacturer's instructions (Clontech). Nested primers that correspond to sequences near the 5'-end of the 1.6 kb fragment are Primer 4: 5'-TGTGGTGTCTGGGCTGCTCTCAGATGC-3' (SEQ ID NO:8) and Primer 5: 5'-ACTGTCTGCTTGGTCCAGTCTCTGG-3' (SEQ ID NO:9). The remaining primers in the nested PCR reactions correspond to portions of the RACE-PCR adaptors synthesized by Clontech and included in the commercially available Marathon cDNA amplification kit, which is used to perform the process of nested PCR.

Nested-PCR was performed, with the first round of PCR performed at 95° C./5 min, followed by 40 cycles of 95° C./45 s, 60° C./45 s, 72° C./2 min and final extension at 72° C./10 min. The second, nested round of PCR was performed under identical conditions except that 35, rather than 40 cycles, were employed. PCR products were cloned into the Invitrogen pCR 2.1 vector for sequence analysis.

An approximately 900 bp mTll-2 5' RACE-cDNA clone was obtained that encoded part of the proregion and all of the signal peptide, and contained about 360 bp of 5' untranslated sequences.

Initially, 3' RACE PCR did not provide additional 3' sequences of the human mTll-2 gene. Therefore, an intermediate PCR amplification step was employed using two nested primers (primer 6: 5'-TACCTGGAAGTCCGGGATGGCCCCACG-3' (SEQ ID NO:10) and primer 7, 5'-GAGGATGTGAAATCGAGCTCCAACAGAC-3' (SEQ ID NO:11)) corresponding to sequences at the 3' end of the 1.6 kb cDNA and four alternative degenerate oligonucleotide primers corresponding to an amino acid sequence conserved in CUB domain 5 of human and mouse mTld and mTll-1 proteins. The degenerate reverse primers 8–11 share the sequence 5'-RAANCCYTTYTTNNNDATNGT-3', but six additional 3' end bases varied among each primer. The terminal sequences of reverse primers 8–11 are: primer 8, 5'-GTCGTC-3'; primer 9, 5'-ATCATC-3'; primer 10, 5'-GTCATC-3'; and primer 11, 5'-ATCGTC-3'. These four degenerate primers are listed as a single degenerate primer in SEQ ID NO:12, wherein the variation among primers 8, 9, 10 and 11 are reflected in the degeneracy in the six 3'-most bases.

Human placenta Marathon-Ready cDNA was used as template (0.5 ng). The first round of PCR was performed at 95° C./5 min followed by 40 cycles of 95° C./45 s, 60° C./45 s, 72° C./4 min, with final extension at 72° C./10 min. The second, nested round of PCR was performed under identical conditions except that 35, rather than 40 cycles were employed.

A specific product of approximately 1.3 kb was excised from a 0.8% agarose gel and was cloned into pCR 2.1 for sequence analysis. The 1.3 kb fragment encoded all of the EGF1, CUB3, EGF2, and CUB4 domains and most of the CUB5 domain of human mTll-2 and was obtained using degenerate reverse primer 10, but not primers 8,9 or 11, in combination with nested forward primers 6 or 7.

To obtain the remaining human mTll-2 cDNA sequences, a 3' RACE PCR was performed using two nested primers corresponding to sequences near the 3'-end of the 1.3 kb fragment (Primer 12, 5'-CAACAACTACCCGAGCGAGGCCCG-3' (SEQ ID NO:13) and primer 13, 5'-GAAGCCTACGACGGCTACGACAGCTC-3' (SEQ ID NO:14)), 0.5 ng human placenta Marathon-Ready cDNA as template (0.5 ng), and the Marathon cDNA Amplification Kit, using the manufacturer's instructions (Clontech). Nested-PCR was performed, with the first round of PCR performed at 95° C./5 min followed by 40 cycles of 95° C./45 s, 60° C./45 s, 72° C./4 min, and final extension at 72° C./10 min. The second, nested round of PCR was performed under identical conditions except that 35, rather than 40, cycles were employed. A specific product of approximately 1.7 kb (encoding part of the CUBS domain and containing 1.6 kb of 3' untranslated region, including a poly A tail) was excised from a 0.8% agarose gel and cloned into pCR 2.1 for sequence analysis.

Murine mTll-2

The same degenerate primers and PCR conditions used to obtain the initial human 375 bp fragment (see above) were used to obtain a heterogeneous product of about 375 bp from mouse cDNA. In this case, the template used was 0.5 ng 7 day post coitus (dpc) mouse embryo Marathon-Ready cDNA (Clontech). The 375 bp PCR product was electrophoresed, excised from a 2% agarose gel, ligated into pCR 2.1, and the ligation reaction restricted with ApaI to reduce the background of BMP-1/mTld clones. In contrast to human sequences, a 375 bp mTll-2 PCR product was obtained using primer 1, in combination with primer 3, but no mTll-2 or other novel products were obtained using primer 2 in combination with primer 3.

Screening of murine 7 dpc and 17 dpc cDNA libraries with the 375 bp fragment failed to generate any positive mTll-2 clones. To obtain all sequences between the 375 bp fragment and the 5' end of murine mTll-2 cDNA sequences, 5' RACE PCR was performed using degenerate reverse primer 3 (above) and a nested primer (primer 14, 5'-GCTTTCCTCATCTGTCCTCTCTACG-3' (SEQ ID NO:15)) corresponding to sequences near the 3'-end of the 375 bp fragment, 0.5 ng of 7 dpc mouse embryo Marathon-Ready cDNA as template, and the Marathon cDNA Amplification Kit, using the manufacturer's instructions (Clontech). Nested-PCR was performed, with the first round of PCR performed at 94° C./30 s, followed by 5 cycles of 94° C./5 s, 72° C./4 min; 5 cycles of 94° C./5 s, 70° C./4 min; 30 cycles of 94° C./5 s, 68°C./4 min and final extension at 72° C./10 min. The second, nested round of PCR was performed at 94° C./30 s, followed by 5 cycles of 94° C./5 s, 72° C./4 min; 5 cycles of 94° C./5 s, 70° C./4 min; 25 cycles of 94° C./5 s, 68° C./4 min and final extension at 72° C./10 min.

PCR products were cloned into Invitrogen pCR 2.1 vector for sequence analysis. A ~900 bp mTll-2 PCR product was obtained that encoded part of the protease domain, all of the signal peptide and proregion and contained ~200 bp of 5' untranslated sequences.

To obtain sequences between the 375 bp fragment and the 3' end of murine mTll-2 cDNA sequences, 3' RACE PCR was performed using degenerate forward primer 1 (above) and a nested primer (primer 15, CCTGTGTGACCTTCGTAGAGAGG-3' (SEQ ID NO:16) corresponding to sequences near the 5' end of the 375 bp fragment. PCR conditions were identical to those used for 5' RACE of murine mTll-2 sequences (above). PCR products were cloned into pCR 2.1 for sequence analysis. A ~1,200 bp mTll-2 PCR product was obtained the encoded part of the protease domain, all of domains CUB1, CUB2, EGF1, CUB3, EGF2 and ended within the CUB3 domain. The remaining portions of the coding sequence were amplified by PCR using oligonucleotide primers designed using sequence information obtained from the 1200 bp fragment. The full length coding region of the murine mTll-2 gene has been determined and occurs between bp 191 and 3229 or SEQ ID NO:3.

Chromosomal Assignment. TLL2 mapping was performed by radiation hybrid mapping (Walter et al., 1994) involving polymerase chain reaction (PCR) analysis of the Genebridge 4 radiation hybrid panel, obtained from Research Genetics. Forward primer 5'-TGGGAGCTGAGCAATGCTAACTGC-3' (SEQ ID NO:17) and reverse primer 5'-GAAGGTGTTCCGGGCGTAGTGCAT-3' (SEQ ID NO:18), corresponding to sequences in TLL2 intron 6 and exon 7, respectively, yielded a 1.4 kb PCR product with human genomic DNA template, but no product with control Chinese hamster genomic DNA template. The PCR was performed with 100 ng of template DNA and 10 pmoles of each primer with a thermocycler program of 95° C. for 5 min, followed by 30 cycles of 95° C./45 s, 65° C./45 s, 72° C./3 min and final extension at 72° C./10 min.

PCR products were electrophoresed on a 0.8% agarose gel, visualized with ethidium bromide and the scoring submitted to the WICGR Mapping Service at the Whitehead Institute/MIT Center for Genome Research. TLL2 clearly mapped on the GeneBridge 4 Panel radiation hybrid set to chromosome 10q, 8.66 cR from marker D10S571 with a Lod score of 15. Additionally, TLL2 was mapped to chromosome 10 by fluorescence in situ hybridization (FISH) on male metaphase chromosome spreads by the method of Trask (1991). A 10 kb BamHI genomic fragment containing TLL2 exons was subcloned into pBluescript II KS+ and labeled with digoxygenin-11-dUTP (Boehringer Mannheim) by random priming. Images were obtained and analyzed as described (Takahara et al. 1994). Double fluorescent signals on both chromosomes were found only at 10q24 in 75% of metaphase spreads examined (15/20) and on no other chromosome (not shown) localizing TLL2 to this region.

Tissue Sections for in situ Hybridization

Tissue sections will be mounted on slides for in situ hybridization. Mouse tissues will be fixed and embedded, as in Lyons et al., "The expression of myosin genes in developing skeletal muscle," *J. Cell Biol.* 111:1465–1476 (1990). Briefly, tissues are fixed in 4% paraformaldehyde in phosphate-buffered saline, dehydrated, and infiltrated with paraffin. Serial sections, 5–7 µm thick, are mounted on gelatinized slides. One to three sections are mounted/slide, deparaffinized in xylene, and rehydrated. Sections are digested with proteinase K, post-fixed, treated with triethanolamine/acetic anhydride, washed, and dehydrated.

In situ hybridization and Washing Procedures

Sections are hybridized overnight at 52° C. in 50% deionized formamide, 0.3 M NaCl, 20 mM Tris-HCl, pH 7.4, 5 mM EDTA, 10 mM NaPO$_4$, 10% dextran sulfate, 1×Denhardt's solution, 50 µg/ml total yeast RNA, 25 µmol/ml thio-ATP (Boehringer-Mannheim), and 50–75,000 cpm/µl $^{35}$S-labeled cRNA probe. Tissue is stringently washed at 65° C. in 50% formamide, 2×SSC, 10 mM dithiothreitol; rinsed in phosphate-buffered saline; and treated with 20 µg/ml RNase A at 37° C. for 30 min. Following washes in 2×SSC and 0.1×SSC for 15 min at 37° C., slides are dehydrated, dipped in Kodak NTB-2 nuclear track emulsion, and exposed for 1 week in light-tight boxes with desiccant at 4° C. Photographic development is in Kodak D-19. Slides are analyzed using light- and dark-field optics of a Zeiss Axiophot microscope.

Subcloning and expression of mTll-2 gene

The mature active forms of BMP-1, mTld, mTll-1 and mTll-2 are all similar in their amino acid sequences. An exception to this is the C-terminus of each protein, where no homology is observed. This uniqueness of C-terminal sequences can been put to use in producing a set of polyclonal antibodies capable of discriminating between the protein forms. In the case of mouse mTll-2, a synthetic peptide that corresponds to the final 17 amino acids of mTll-2 can be linked to the protein carrier Keyhole Limpet Hemocyanin, suspended in saline and emulsified by mixing with an equal volume of Freund's adjuvant and injected into three to four subcutaneous dorsal sites in each of two rabbits. Bleeds for sera are at 12 and 16 weeks after immunization and boosts. Such antibodies have commercial utility in an assay for visualizing the production and localization of mTll-2 protein in cells, tissues, and mammalian organisms, including, but not limited to model systems (e.g., rodents, primates, and the like) as well as humans.

It should be noted that unique sequences exist in the protease, CUB and proregions of these proteins and can be used to detect and distinguish among the various members of the family. See, Lee, S. *J. Biol. Chem.* 272:19059–19066 (1997).

In view of the rapid pace at which the understanding of the bone morphogenetic proteins is advancing, the ability to distinguish individual components one from another is important, not merely from a research perspective, but in monitoring the level and distribution of BMP system components in patients having disorders of the BMP system. Such disorders could include, for example, in mice and humans, fibrotic conditions or heart disease. In addition, hereditary developmental abnormalities may be due to defects in the TLL2 gene. Determining the role of mTll-2 in such genetic abnormalities will be enabled by the antibody and nucleic acid probes described herein. The mTll-2 protein is quite clearly important in organism development, in that it is expressed in placenta and in the developing heart.

We claim:

1. An isolated polynucleotide comprising a polynucleotide encoding a polypeptide having an amino acid sequence selected from the group consisting of SEQ ID NO:2 and SEQ ID NO:4.

2. The polynucleotide of claim 1 comprising nucleotides 365 to 3409 of SEQ ID NO:1.

3. The polynucleotide of claim 1 comprising SEQ ID NO:1.

4. The polynucleotide of claim 1 comprising nucleotides 191 to 3229 of SEQ ID NO:3.

5. The polynucleotide of claim 1 comprising SEQ ID NO:3.

6. An expression vector comprising a transcriptional promoter operably linked to the polynucleotide of claim 1.

7. The expression vector of claim 6 wherein the polynucleotide comprises nucleotides 365 to 3409 of SEQ ID NO:1.

8. The expression vector of claim 6 wherein the polynucleotide comprises SEQ ID NO:1.

9. The expression vector of claim 6 wherein the polynucleotide comprises nucleotides 191 to 3229 of SEQ ID NO:3.

10. The expression vector of claim 6 wherein the polynucleotide comprises SEQ ID NO:3.

11. A host cell comprising the expression vector of claim 6.

12. An isolated polynucleotide complementary to the polynucleotide of claim 1 over the full length of the polynucleotide of claim 1.

13. A host cell comprising a polynucleotide of claim 1.

14. A method of producing a polypeptide comprising an amino acid sequence selected from the group consisting of SEQ ID NO:2, and SEQ ID NO:4, the method comprising:

culturing the host cell of claim 13 under conditions suitable for expressing the polypeptide; and recovering the polypeptide.

15. The polynucleotide of claim 1 comprising a polynucleotide that encodes SEQ ID NO:2.

16. The polypeptide of claim 1 comprising a polynucleotide that encodes SEQ ID NO:4.

17. An isolated polynucleotide that hybridizes to a nucleic acid sequence selected from the group consisting of SEQ ID NO:1 and SEQ ID NO:3 under the following conditions: hybridization at 65° C. for 18 hours followed by a first wash in 2×SSC, 0.1% SDS for 30 minutes at room temperature, a second wash in 2×SSC, 0.1% SDS for 30 minutes at 65° C. for 30 minutes and a third wash in 1×SSC, 0.1% SDS at 65° C. for 30 minutes, wherein the isolated polynucleotide encodes a polypeptide that cleaves prolysyl oxidase.

* * * * *

UNITED STATES PATENT AND TRADEMARK OFFICE
CERTIFICATE OF CORRECTION

PATENT NO.    : 6,579,702 B2
DATED         : June 17, 2003
INVENTOR(S)   : Daniel S. Greenspan, Ian C. Scott and Christina L. Thomas It is certified that error appears in the above-identified patent and that said Letters Patent is hereby corrected as shown below:

<u>Column 1,</u>
Lines 6-10, please delete the entire paragraph and insert therefor the following:

-- This invention was made with United States government support awarded by the following agencies:

NIH AR43621; GM46846
The United States has certain rights in this invention. --

Signed and Sealed this

Sixteenth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,579,702 B2
DATED : June 17, 2003
INVENTOR(S) : Daniel S. Greenspan, Ian C. Scott and Christina L. Thomas It is certified that error appears in the above-identified patent and that said Letters Patent is hereby corrected as shown below:

<u>Title page,</u>
Item [73], Assignee, should read -- Wisconsin Alumni Research Foundation. --

Signed and Sealed this

Twentieth Day of July, 2004

JON W. DUDAS
*Acting Director of the United States Patent and Trademark Office*